(12) United States Patent
Bew et al.

(10) Patent No.: US 10,259,784 B2
(45) Date of Patent: *Apr. 16, 2019

(54) METHOD AND CATALYST FOR SYNTHESISING AZIRIDINE

(71) Applicant: University of East Anglia, Norwich (GB)

(72) Inventors: Sean Patrick Bew, Norwich (GB); Sean Michael Thurston, Norwich (GB); Paolo Pesce, Noicattaro (IT)

(73) Assignee: University of East Anglia, Norwich (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/675,982

(22) Filed: Aug. 14, 2017

(65) Prior Publication Data

US 2017/0342030 A1   Nov. 30, 2017

Related U.S. Application Data

(63) Continuation of application No. 14/404,123, filed as application No. PCT/GB2013/051449 on May 31, 2013, now Pat. No. 9,732,034.

(30) Foreign Application Priority Data

Jun. 1, 2012   (GB) .................................. 1209840.6

(51) Int. Cl.
| | | |
|---|---|---|
| *C07D 203/02* | (2006.01) | |
| *C07D 203/14* | (2006.01) | |
| *C07D 203/18* | (2006.01) | |
| *C07D 203/22* | (2006.01) | |
| *B01J 31/02* | (2006.01) | |
| *C07D 203/08* | (2006.01) | |
| *C07D 403/04* | (2006.01) | |
| *C07D 413/06* | (2006.01) | |
| *C07F 9/24* | (2006.01) | |

(52) U.S. Cl.
CPC ........ *C07D 203/02* (2013.01); *B01J 31/0264* (2013.01); *C07D 203/08* (2013.01); *C07D 203/14* (2013.01); *C07D 203/18* (2013.01); *C07D 203/22* (2013.01); *C07D 403/04* (2013.01); *C07D 413/06* (2013.01); *C07F 9/2483* (2013.01); *C07B 2200/05* (2013.01)

(58) Field of Classification Search
CPC .................................................. C07D 203/02
USPC ....................................................... 546/268.1
See application file for complete search history.

(56) References Cited

U.S. PATENT DOCUMENTS 9,732,034 B2 * 8/2017 Bew ..................... C07D 203/02

FOREIGN PATENT DOCUMENTS

WO   WO 00/56708   9/2000

OTHER PUBLICATIONS

Hashimoto, Journal of the American Chemical Society (2011), 133(25), 9730-9733.*
Schenker et al. European Journal of Organic Chemistry, 2011, 2209-2222.*
Afforunato, et al, J. Org. Chem, 2008, vol. 73, p. 9214-9220.
Akiyama, et al., Organic Letters, 2009, vol. 11(11), pp. 2445-2447.
Antilla, et al, Angew. Chem. Int. Ed., 2000, vol. 39(24), pp. 4518-4520.
Baret, et al., Bull. Soc. Chem. Fr. 1972, p. 825.
Baret, et al., Bull. Soc. Chem. Fr. 1972, pp. 2493-2500.
Bew, et al., Advanced Synthesis and Catalysis, 2009, vol. 351, pp. 2579-2599.
Bew, et al., Organic Letters, 2009, vol. 11, p. 4552,4555.
Capriati, et al, Organic Letters, 2005, vol. 7, pp. 3749-3752.
Concelllon, et al., Angew. Chem. Int. Ed. 2004, 43, pp. 4333-4336.
Concellon, et al., Chem. Eur. J., 2005, vol. 11., pp. 4492-4501.
Dallas, et al., J. Chem. Soc. 1970, pp. 2383-2394.
Davies, et al, Beilstein Journal of Organic Chemistry, 2011, vol. 7, pp. 839-846.
Freedman, et al., Journal of the American Chemical Society, 1987, vol. 109, pp. 4727-4728.
Han, et al., Journal of the American Chemical Society, No. 134, 2012, pp. 6532-6535.
Hansen, et al, Angew, Chem. Int. Ed. Engl., 1995., vol. 34, pp. 676-678.
Hashimoto, et al., Journal of the American Chemical Society, vol. 133, 2011, pp. 9730-9733.
International Search Report and Written Opinion from related International Application No. PCT/GB2013/051449, dated Aug. 22, 2013, 13 pages.
International Preliminary Report on Patentability from related International Application No. PCT/GB2013/051449, dated Dec. 2, 2014, 9 pages.
Jiao, et al, Angewandte Chemie, Int Ed., vol. 47(13), 2008, pp. 2411-2413.
Juhl, et al., J. Chem. Soc., Perkin Trans 1, 1999, pp. 2293-2297.
Lin, et al, Physical Chemistry Chemical Physics, vol. 14, 2012, pp. 3669-3680.
Lown et al, Canadian Journal of Chemistry, No. 47, 1969, pp. 4335-5345.
March, Advanced Organic Chemistry, John Wiley & Sons, 4th Edition, 1992, p. 495.
Muller, et al, Helvetica Chemica Acta, vol. 87, 2004, pp. 227-239.
Nagel, et al., J. Org. Chem., vol. 36, 1971, pp. 3911-3917.

(Continued)

*Primary Examiner* — Nizal S Chandrakumar
(74) *Attorney, Agent, or Firm* — Barnes & Thornburg LLP; Scott Rothenberger

(57) ABSTRACT

The present invention relates to methods of synthesizing aziridines including isotopically labelled aziridines, said methods comprising contacting an imine or one or more precursors thereof with a diazo compound in the presence of a phosphoramide or a phosphoramide-derived catalyst. The present invention also relates to aziridines, modified aziridines and aziridine-derived compounds preparable by the aforementioned methods, and to phosphoramide or phosphoramide-derived catalysts suitable for use in such methods.

21 Claims, No Drawings

(56) References Cited

OTHER PUBLICATIONS

Nakashima, et al., Journal of the American Chemical Society, vol. 128(30), 2006, pp. 9626-9627.
Nakashima, et al., Journal of the American Chemical Society, vol. 128(30), 2006, pp. 9626-9627, Supporting Information, pp. 1-4.
Ochiai, et al., J. Org. Chem., vol. 64, 1999, pp. 3181-3189.
Padwa, et al., Journal of the American Chemical Society, vol. 93, 1971, pp. 1400-1408.
Rueping, et a., Angewandte Chemie, Int Ed., vol. 47(26), 2008, pp. 6798-6801.
Satoh, et al., Tetrahedron Letters No. 39, 1998, pp. 2345-2348.
Satoh, et al, Tetrahedron, vol. 56, 2000, pp. 4415-4425.
Satoh, et al., Tetrahedron, vol. 59, 2003, pp. 9803-9810.
Schenker, et al., Eur J. Org. Chem, 2011, pp. 2209-2222.
Troisi. et al. Eur. J. Org. Chem., 2006, pp. 775-781.
Tung, "The Developmen of Deuterium-Containing Drugs", Innovations in Pharmaceutical Technology, Issue 32, 2010, pp. 1-4.
Vallalath, et al., Angewandte Chemie, Int. Ed., vol. 49(50), 2010, pp. 9749-9752.
Wakchaure, et al., Angewandte Chemie, Int Ed., vol. 49(24), 2010, pp. 4136-4139.
Wenkert, et al., J. Org. Chem., vol. 50, 1985, pp. 4114-4119.
Williams et al., Journal of the American Chemical Society, No. 126, 2004, pp. 1612-1613.
Woller, et al., Journal of Organic Chemistry, vol. 95, No. 4, 1970, pp. 888-898.
Zeng, et al, Organic Letters, vol. 11(14), 2009, pp. 3036-3039.
Bew et al, Chem 1, 921-945, 2016.

\* cited by examiner

METHOD AND CATALYST FOR SYNTHESISING AZIRIDINE

This application is a continuation application of U.S. Patent Application Ser. No. 14/404,123, filed Nov. 26, 2014, which is a national stage application under 35 U.S.C. § 371 of International Application No. PCT/GB2013/051449, filed May 31, 2013 and published as WO 2013/179052 A1 on Dec. 5, 2013, which claims the benefit of GB 1209840.6, filed Jun. 1, 2012, the contents of which are incorporated herein by reference in its entirety.

TECHNICAL FIELD

The present invention relates to methods of synthesising aziridines including isotopically labelled aziridines, said methods comprising contacting an imine or one or more precursors thereof with a diazo compound in the presence of a phosphoramide or a phosphoramide-derived catalyst. The present invention also relates to aziridines, modified aziridines and aziridine-derived compounds preparable by the aforementioned methods, and to phosphoramide or phosphoramide-derived catalysts suitable for use in such methods.

BACKGROUND OF THE INVENTION

Aziridines are basic, three-membered nitrogen containing heterocycles that resemble their oxygen counterpart epoxides in terms of chemical reactivity and structure. Aziridines like other three membered ring-systems are highly strained with ~60° bond angles. As a consequence, aziridines undergo highly regio- and stereoselective transformations. Due to their utility aziridines are highly sought after useful entities that are frequently employed by synthetic chemists in agrochemical, pharmaceutical, medicinal, materials and academic laboratories alike. Further substantiating their pre-eminence, aziridines are often employed as key intermediates in the synthesis of unnatural α- and β-amino acids, chiral auxilaries, polymers, azasugars and heterocyclic entities such as oxazolidinones, imidazolidines, β-lactams, thioxazolidenethiones and pyrrolidines. Furthermore, aziridines are powerful alkylating agents. Many synthetic and natural product derived aziridines have potent anti-tumour, anti-viral and/or anti-bacterial properties, examples being the Azinomycins, Ficellomycin, Miraziridine, Maduropeptin, PBI-A, Mitomycin A, FR66979 and NSC 639823. Therefore the development of aziridine syntheses that are efficient, high yielding, mild, environmentally friendly and amenable to the formation of structurally diverse entities is extremely important.

Accordingly, a plethora of racemic and optically active synthetic protocols have been developed for the generation of aziridines. In the main the synthetic approaches can be categorised as: cyclisation reactions, transfers of nitrogen to olefins, transfers of carbon to imines, additions across the carbon-nitrogen double bond of azirines, reactions of ylids, aza-Darzen approaches, ring contraction and functional group transformations. Of these, aziridination via carbene transfer to N-substituted imines has proven particularly popular.

The reaction of a carbene with a Schiff base to afford an aziridine has been known since the 1970s. Baret el al. (Bull. Soc. Chem. Fr., 1972, p. 2493) reported aziridine formation when an imine was allowed to react with ethyl diazoacetate in the presence of copper powder. Similarly, performing a Simmons-Smith reaction incorporating an imino ester also afforded aziridines (Baret et al., Bull. Soc. Chem. Fr., 1972, p. 825).

The methodology has since been extended to chiral synthesis. For example, in 1995 Hansen et al. (Angew. Chem. Int. Ed. Engl., 1995, vol. 34, p. 676) reported that ethyl diazoacetate reacted with diphenylimine in the presence of a catalytic quantity of a chiral non-racemic copper(I) bis (oxazoline) complex 1 [derived from (S)-phenylglycine].

Scheme 1

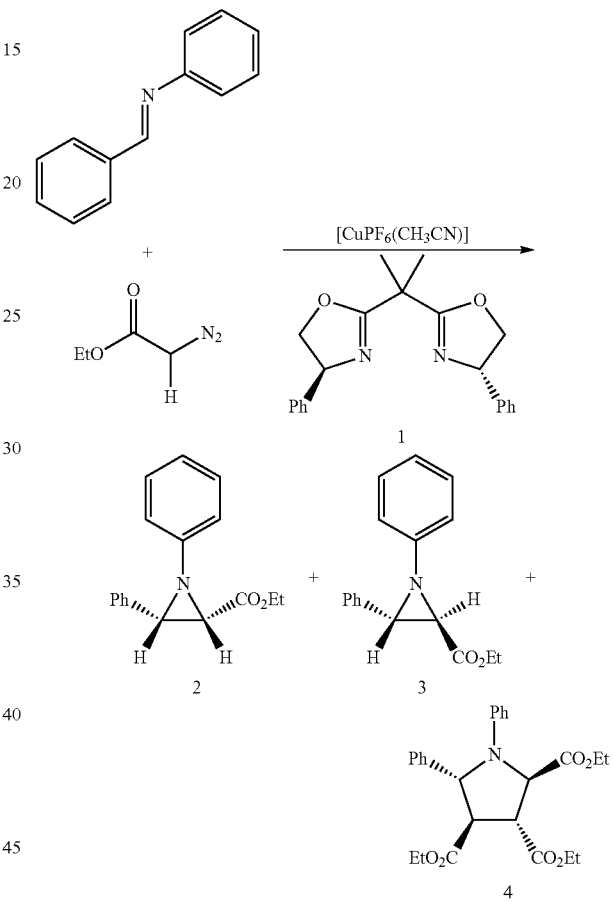

The reaction afforded the desired chiral non-racemic N-phenylaziridines as their cis-/trans-diastereoisomers (2 and 3 respectively, Scheme 1) with modest stereoinduction (22-67% e.e.). In addition to the desired aziridines, varying amounts (i.e. ~10%) of a racemic pyrrolidine 4 was generated as an unwanted by-product (Scheme 1). Further drawbacks to this procedure are the incorporation of the toxic and hence environmentally unfriendly copper salt and the fact that cleavage of the N-phenyl substituent, affording the corresponding NH-aziridine, without recourse to ring-opening the aziridine ring is extremely challenging.

Stemming from the above, a wide range of metal based Lewis acids have been employed for the activation and subsequent reaction of N-substituted imines with alkyl diazoacetates to afford the corresponding aziridines in 42-93% yields. Examples of the Lewis acids that have been investigated include aluminium chloride, titanium(IV) chloride, tin(IV) chloride, methylrhenium trioxide, lanthanide triflates, indium trichloride, $[(\eta^2\text{-}C_3H_5)Fe(CO)_2(THF)]^+$ $BF_4^-$ and $[Mo(OTf)(\eta^3\text{-}C_3H_5)(CO)_2(phen)]$.

The use of such catalysts however incurs a number of serious draw-backs such as the generation of metal-contaminated waste which may well present potential disposal issues and increase the environmental impact of the chemistry. In general many of the metal-mediated processes have limited substrate scope potential, and many require relatively high loadings of the metal salt and/or the ligand, a fact that further exacerbates disposal and environmental problems, and increases the overall costs of the chemistry undertaken. Additionally many of the metals employed are toxic, difficult to handle and store and would, if an accident were to occur, present significant health and disposal problems. Due to their often highly reactive nature towards water or damp air, the reaction conditions for their use require absolutely anhydrous reaction conditions to be maintained at all times, otherwise significantly reduced yields result. Furthermore, the reactive nature of these Lewis acids often results in significant degradation of the aziridines giving lower yields. The knock on effect of this is that subsequent purification of the desired products can be complicated, a fact that again increases the environmental impact of aziridine synthesis.

In view of the above, a few researchers have sought to avoid the difficulties associated with the use of metal based Lewis acid catalysts by employing organic molecules as 'organocatalysts', albeit with varying success. Many of these 'organic mediated' procedures are also not ideal and the majority have severe experimental and/or substrate limitations.

Taking the lead in this field, Antilla et al. (Angew. Chem. Int. Ed., 2000, vol. 39(24), pp. 4518-4520) have reported a procedure (Scheme 2) that requires the synthesis of an expensive precatalyst 5 (~£450 per mmol) that is only usable when transformed into its active form 6. From a practical point of view it would be preferable that the catalyst 6 be stable and storable in a bottle, on a shelf ready to be used as and when required; unfortunately this is not the case. The procedure further requires the use of relatively high (~10 mol %) amounts of catalyst and the transformation of 5 into 6 is also demanding requiring 3-4 equivalents of the triphenylborate.

Scheme 2

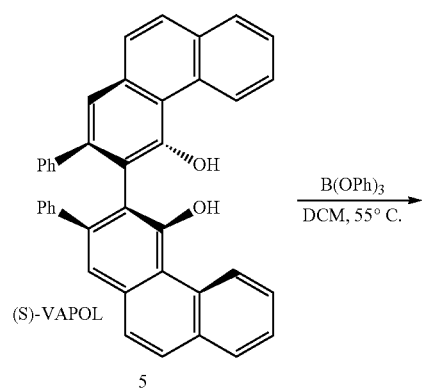

(S)-VAPOL
5

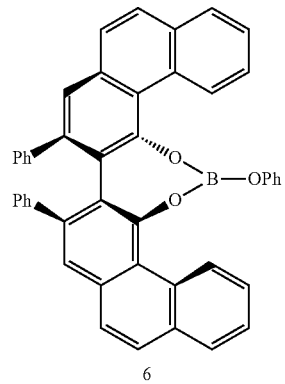

Others, such as Akiyama et al. (Organic Letters, 2009, vol. 11(11), pp. 2445-2447) and Zeng et al. (Organic Letters, 2009, vol. 11(14), pp. 3036-3039) have employed chiral phosphoric acids as catalysts, as illustrated below (Schemes 3 and 4).

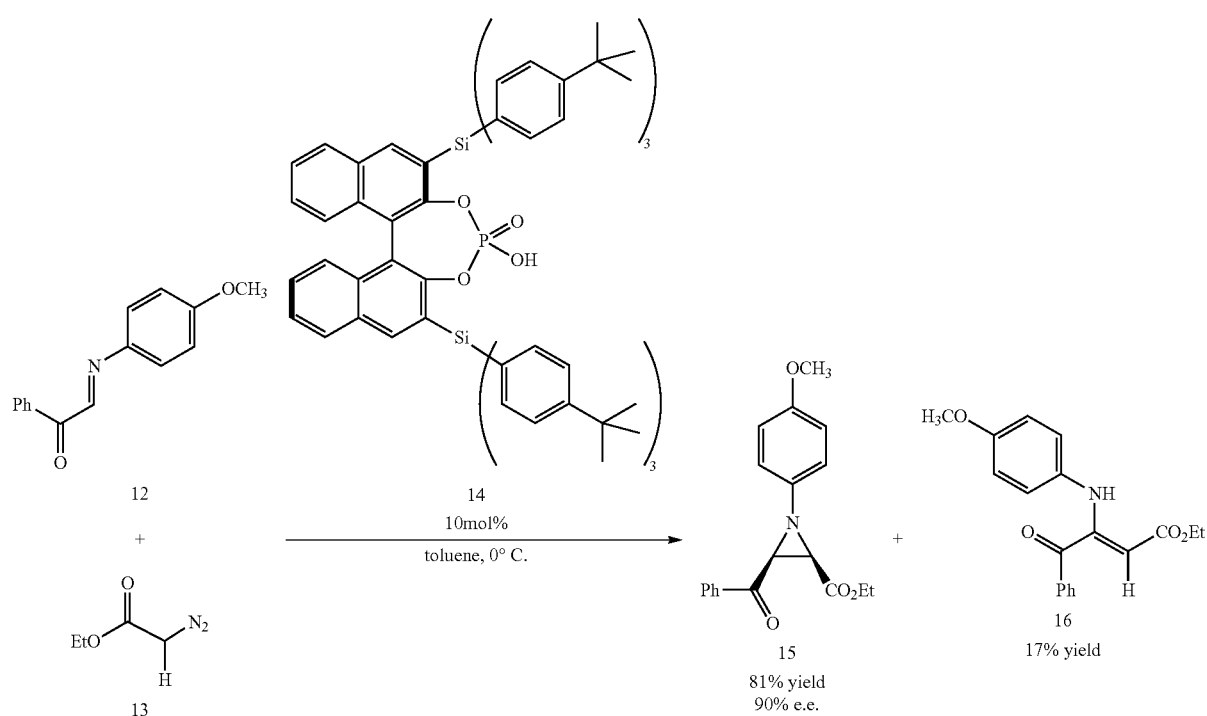
Scheme 3
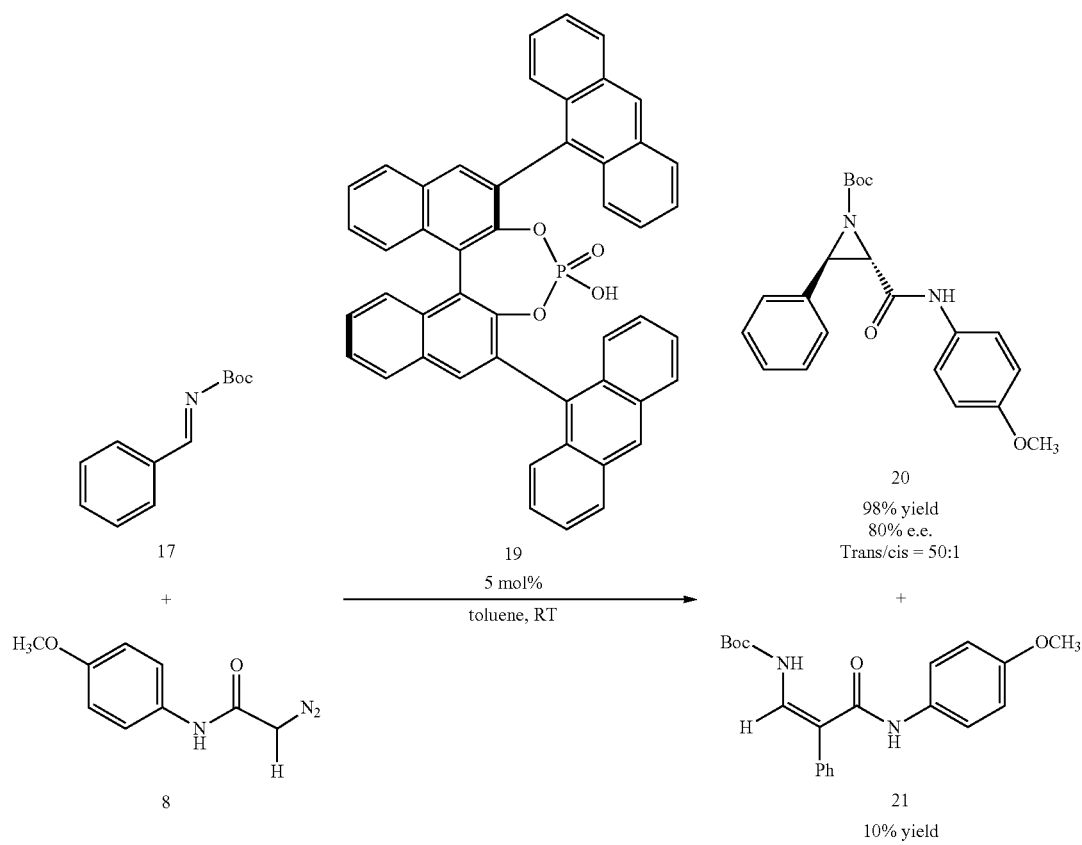
Scheme 4
Whilst the use of chiral phosphoric acids overcomes some of the storage problems associated with the Antilla procedure, a number of other difficulties still remain. In particular, the efficacy of the chiral phosphoric acids is highly dependent upon the nature of the starting material substrates. For instance the reaction will not proceed where a group such as a benzyl group is attached to the nitrogen atom of the imine. This in turn can lead to the use of N-protecting groups such as Boc groups which are difficult to remove without ring-opening the aziridine.

Furthermore, the phosphoric acid catalyst often results in significant degradation of the desired aziridines. Indeed, in the procedure set out by Zeng et al., high percentages of undesired enamine species such as 21 are generated. Thus careful purification and/or dilute reaction conditions are required, a fact that again increases the environmental impact and, inevitably, results in lower yields of the desired aziridines.

In view of the above, there is a need for further methods of synthesising aziridines to be developed, which avoid the use of metal based Lewis acid catalysts yet also overcome many of the disadvantages associated with the organocatalytic techniques discussed above.

One technique, disclosed by Hashimoto et al. (Journal of the American Chemical Society, 2011, vol. 133, pp. 9730-9733), employs the use of a chiral N-triflyl phosphoramide to catalyse the synthesis of trisubstituted azirdines from N-α-diazoacyl oxazolidinones and N-boc imines.

There is also a need for methods or synthesising isotopically labelled aziridines which allow for the regio- and stereo-specific introduction of isotopic labels into the aziridine ring, or into groups attached to the aziridine ring. Isotopically labelled compounds so-produced would find particular application in the field of nuclear medicine and/or pharmacological studies.

A particular challenge is the stereo-specific synthesis of aziridines that have pseudo-meso isotopic stereoisomers. In other words, the stereo-specific synthesis of aziridines that would be identical meso compounds were it not for their isotopic labelling. Such otherwise identical isotopic stereoisomers cannot be separated by conventional purification techniques, such as by chiral chromatography, diastereomeric crystallisation and the like, since such techniques cannot differentiate between the labelled and non-labelled atomic positions. Accordingly, stereo-specific synthesis is of vital importance if pseudo-meso isotopic stereoisomers are to be obtained in a high degree of purity.

SUMMARY OF THE INVENTION

Accordingly, a first aspect of the present invention relates to a method of synthesising aziridine (III) or a salt thereof, said method comprising contacting imine (I), or a salt or one or more precursors thereof, with a diazo compound (II) or a salt thereof in the presence of a catalyst:

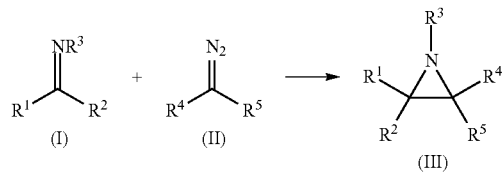

wherein $R^1$, $R^2$, $R^3$, $R^4$ and $R^5$ each independently represent any atom or group, and wherein the catalyst is a compound of formula (IV) or a salt thereof, or a compound of formula (V) or a salt thereof:

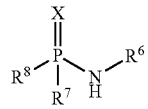

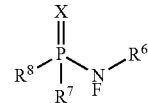

wherein X is O, S or $NR^9$, and $R^6$, $R^7$, $R^8$ and $R^9$ each independently represent any atom or group.

In one embodiment of the first aspect of the present invention, the imine (I), one or more precursors thereof, and/or the diazo compound (II) are isotopically labelled such that the resultant aziridine (III) is also isotopically labelled.

In one embodiment of the first aspect of the present invention, the catalyst is a chiral compound of formula (IV) or a salt thereof, or a chiral compound of formula (V) or a salt thereof. Alternatively the compound of formula (IV) or (V) may be a chiral.

Preferably the catalyst is a compound or formula (IV) or a salt thereof.

In one embodiment of the first aspect of the present invention, the catalyst is attached to a solid support. For example, the solid support may be a polymeric resin such as polystyrene resin, a Wang resin, a Tentagel™ resin, a metal organic framework (MOF), an inorganic support such as silica, mesoporous silica or clays such as montmorillonite, or a dendrimer. Preferably the solid support is a polymeric resin such as polystyrene resin.

In one embodiment of the first aspect of the present invention, the method comprises contacting the imine (I) or the salt thereof with the diazo compound (II) or the salt thereof in the presence of the catalyst. The method may further comprise the step of synthesising the imine (I). For example, the imine (I) or the salt thereof may be synthesised from an amine $H_2NR^3$ or a salt or protected derivative thereof, and a carbonyl compound $R^1COR^2$ or a salt or protected derivative thereof.

In one embodiment, the imine (I) or the salt thereof is isolated prior to the reaction with the diazo compound (II) or the salt thereof.

In another embodiment, the imine (I) or the salt thereof is not isolated. For instance, the reaction of the amine $H_2NR^3$ or the salt or protected derivative thereof, and the carbonyl compound $R^1COR^2$ or the salt or protected derivative thereof may occur in the same reaction solvent in which the imine (I) or the salt thereof is contacted with the diazo compound (II) or the salt thereof. Preferably, the reaction of the amine $H_2NR^3$ or the salt or protected derivative thereof, and the carbonyl compound $R^1COR^2$ or the salt or protected derivative thereof, to give the imine (I) or a salt thereof, and the reaction of the imine (I) or the salt thereof with the diazo compound (II) or the salt thereof occur in a 'one-pot' process.

Preferably, the reaction of the amine $H_2NR^3$ or the salt or protected derivative thereof, and the carbonyl compound $R^1COR^2$ or the salt or protected derivative thereof occurs in the presence of an acid such as a Brønsted acid.

Optionally, the reaction of the amine $H_2NR^3$ or the salt or protected derivative thereof, and the carbonyl compound $R^1COR^2$ or the salt or protected derivative thereof occurs in the presence of the catalyst. Alternatively, the catalyst may be added to the reaction mixture after the formation of the imine (I) or the salt thereof.

In another embodiment of the first aspect of the present invention, the method comprises contacting one or more precursors of the imine (I) with the diazo compound (II) or the salt thereof in the presence of the catalyst. The "precursors of the imine (I)" may optionally include salts of the precursors.

Preferably the one or more precursors of imine (I) comprise an amine $H_2NR^3$ or a salt or protected derivative thereof, and a carbonyl compound $R^1COR^2$ or a salt or protected derivative thereof.

For the avoidance of doubt, substituents $R^1$, $R^2$ and $R^3$ of the carbonyl compound $R^1COR^2$ and the amine $H_2NR^3$ are as defined in relation to the imine (I).

As used herein, a "protected derivative" of the carbonyl compound $R^1COR^2$ includes compounds in which the carbonyl group has been protected, for instance as an acetal or a ketal. Preferably the protecting group is acid-labile.

Similarly, a "protected derivative" of the amine $H_2NR^3$ includes compounds in which the amino group has been protected, for instance using an acid-labile protecting group such as a t-butoxycarbonyl (Boc), 2-(4-biphenylyl)-isopropoxycarbonyl (Bpoc), trityl or 2-nitrophenylsulphenyl (Nps) group.

Any "protected derivative" of an amine or a carbonyl compound may optionally be in salt form.

Suitable protecting groups for carbonyl compounds and amines are known in the art, for example from "Protective Groups in Organic Synthesis" by T. W. Greene and P. G. M. Wuts (Wiley-Interscience, 4$^{th}$ edition, 2006).

In one embodiment of the first aspect of the present invention. $R^1$, $R^2$ and $R^3$ are each independently hydrogen, halogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein any two or more of $R^1$, $R^2$ and $R^3$ together with the atom or atoms to which they are attached may form a cyclic hydrocarbyl group which may optionally be substituted and which may optionally include one or more heteroatoms N, O or S in its carbon skeleton.

Preferably $R^1$, $R^2$ and $R^3$ are each independently hydrogen or a hydrocarbyl group comprising from 1 to 30 carbon atoms. More preferably $R^1$, $R^2$ and $R^3$ are each independently hydrogen or a hydrocarbyl group comprising from 1 to 20 carbon atoms. Most preferably $R^1$, $R^2$ and $R^3$ are each independently hydrogen or a hydrocarbyl group comprising from 1 to 12 carbon atoms.

In one embodiment $R^1$ is hydrogen.

In one embodiment $R^2$ is a hydrocarbyl group.

Preferably $R^2$ is a substituted or unsubstituted aryl, arylalkyl, arylalkenyl, arylalkynyl, alkylaryl, alkenylaryl or alkynylaryl group which optionally includes one or more heteroatoms in its carbon skeleton. More preferably $R^2$ is a substituted or unsubstituted aryl group which optionally includes one or more heteroatoms in its carbon skeleton. Most preferably $R^2$ is a substituted or unsubstituted phenyl, naphthyl, pyridyl, quinolyl or isoquinolyl group.

Alternatively $R^2$ may be a substituted or unsubstituted acyl group which optionally includes one or more heteroatoms in its carbon skeleton. More preferably $R^2$ is a $—CO_2R^c$ group wherein $R^c$ is independently hydrogen, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises from 1 to 15 carbon atoms. Preferably $R^c$ is an unsubstituted alkyl, alkenyl, aryl, arylalkyl, arylalkenyl, alkylaryl or alkenylaryl group which optionally includes one or more heteroatoms in its carbon skeleton and preferably comprises from 1 to 12 carbon atoms. Most preferably $R^2$ is a $—CO_2R^c$ group wherein $R^c$ is an unsubstituted alkyl group comprising from 1 to 6 carbon atoms.

Alternatively still $R^2$ may be a substituted or unsubstituted alkyl group which optionally includes one or more heteroatoms in its carbon skeleton. More preferably $R^2$ is a substituted or unsubstituted alkyl group comprising from 1 to 6 carbon atoms, such as a cyclohexyl or t-butyl group.

Where $R^2$ is substituted, preferably it is substituted with one or more of —F, —Cl, —Br, —I, —CF$_3$, —CCl$_3$, —CBr$_3$, Cl$_3$, —OH, —SH, —NH$_2$, —N$_3$, —NH═NH$_2$, —CN, —NO$_2$, —COOH, —R$^a$—O—R$^b$, —R$^a$—S—R$^b$, —SO—R$^b$, —SO$_2$—R$^b$, —SO$_2$—OR$^b$, —O—SO$_2$—R$^b$, —O—SO$_2$—OR$^b$, —R$^a$—N(R$^b$)$_2$, —R$^a$—N(R$^b$)$_3$$^+$, —R$^a$—Si(R$^b$)$_3$, —R$^a$—CO—R$^b$, —R$^a$—CO—OR$^b$, —R$^a$O—CO—R$^b$, —R$^a$—CO—N(R$^b$)$_2$, —R$^a$—NR$^b$—CO—R$^b$, —R$^a$O—CO—OR$^b$, —R$^a$—CS—R$^b$ or —R$^b$; wherein R$^a$ and R$^b$ are as defined below. More preferably where $R^2$ is substituted, it is substituted with one or more of —F, —Cl, —Br, —I, —CN, —NO$_3$, —O—R$^b$ or —R$^b$. Most preferably, where $R^2$ is substituted, it is substituted with one or more of —F, —Cl, —Br, or —CN.

In a preferred embodiment, $R^2$ is a —CO$_2$Et, cyclohexyl, t-butyl, phenyl, pyridyl, chlorophenyl, bromophenyl, iodophenyl, fluorophenyl, 2,4-difluorophenyl, pentafluorophenyl, tolyl,

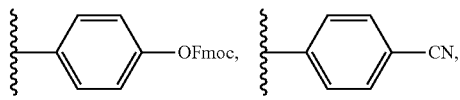

nitrophenyl, naphthyl, quinolyl or isoquinolyl group.

In one embodiment $R^3$ is an electron donating group.

Alternatively or in addition, $R^3$ may be a hydrocarbyl group. Preferably $R^3$ is a substituted or unsubstituted alkyl, alkenyl, aryl, arylalkyl or alkylaryl group which optionally includes one or more heteroatoms in its carbon skeleton, preferably comprising from 1 to 20 carbon atoms. More preferably $R^3$ is a substituted or unsubstituted aryl, arylalkyl or alkylaryl group which optionally includes one or more heteroatoms in its carbon skeleton, preferably comprising from 6 to 12 carbon atoms.

Where $R^3$ is substituted, preferably it is substituted with one or more of —F, —Cl, —Br, —I, —CF$_3$, —CCl$_3$, —CBr$_3$, —Cl$_3$, —OH, —SH, —NH$_2$, —N$_3$, —NH═NH$_2$, —CN, —NO$_2$, —COOH, —R$^a$—O—R$^b$, —R$^a$—S—R$^b$, —SO—R$^b$, —SO$_2$—R$^b$, —SO$_2$OR$^b$, —O—SO$_2$—R$^b$, —O—SO$_2$OR$^b$, —R$^a$—N(R$^b$)$_2$, —R$^a$—N(R$^b$)$_3$$^+$, —R$^a$—Si(R$^b$)$_3$, —R$^a$—SO—R$^b$, —R$^a$—SO—OR$^b$, —R$^a$O—CO—R$^b$, —R$^a$—CO—N(R$^b$)$_2$, —R$^a$—NR$^b$—CO—R$^b$, —R$^a$O—CO—OR$^b$, —R$^a$—CS—R$^b$ or —R$^b$; wherein R$^a$ and R$^b$ are as defined below. More preferably where $R^3$ is substituted, it is substituted with —O—R$^b$.

In another embodiment, where $R^3$ is substituted, it is substituted with one or more of —OH, —OMe, —O$^t$Bu or —NO$_2$.

Most preferably $R^3$ is a —$CH_2CH$=$CH_2$, —$SiMe_3$, n-octyl, t-butyl, benzyl, —$CH(Ph)_2$, —$C(Ph)_3$,

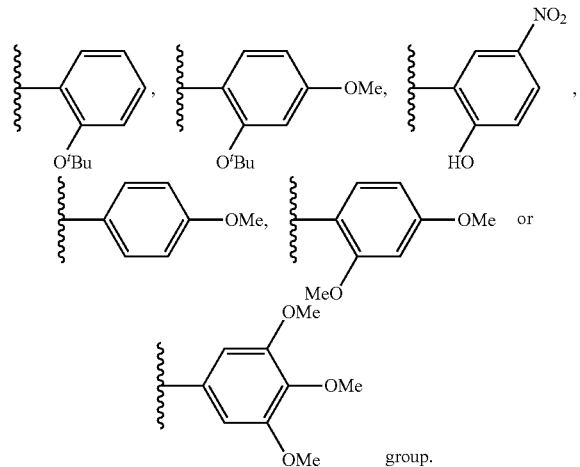 group.

In a preferred embodiment, $R^1$ is hydrogen, $R^2$ is a substituted or unsubstituted alkyl, acyl, aryl, arylalkyl or alkylaryl group which optionally includes one or more heteroatoms in its carbon skeleton, and $R^3$ is a substituted or unsubstituted alkyl, alkenyl, acyl, arylalkyl or alkylaryl group which optionally includes one or more heteroatoms in its carbon skeleton.

In a more preferred embodiment, $R^1$ is hydrogen, $R^2$ is a substituted or unsubstituted aryl group which optionally includes one or more heteroatoms in its carbon skeleton, and $R^3$ is a substituted or unsubstituted aryl, arylalkyl or alkylaryl group which optionally includes one or more heteroatoms in its carbon skeleton.

In one embodiment of the first aspect of the present invention, at least one of $R^1$, $R^2$ and $R^3$ is chiral.

In one embodiment of the first aspect of the present invention, $R^4$ and $R^5$ are each independently hydrogen, halogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein $R^4$ and $R^5$ together with the atom or atoms to which they are attached may form a cyclic hydrocarbyl group which may optionally be substituted and which may optionally include one or more heteroatoms N, O or S in its carbon skeleton.

In one embodiment of the first aspect of the present invention, at least one of $R^4$ and $R^5$ is chiral.

Preferably, $R^4$ and $R^5$ are each independently hydrogen or an electron withdrawing group. More preferably $R^4$ and $R^5$ are each independently hydrogen or a —$NO_2$, —CN, —CO—$R^d$, —CO—$OR^d$, —CO—$N(R^d)_2$, —CS—$R^d$, —CS—$OR^d$, —CS—$N(R^d)_2$, —C=$NR^d$—$N(R^d)_2$, —C=$NR^d$—$R^d$ or —C=$NR^d$—$OR^d$ group, wherein each —$R^d$ is independently hydrogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises from 1 to 15 carbon atoms.

More preferably still $R^4$ and $R^5$ are each independently hydrogen or a —$NO_2$, —CN, —CO—$R^d$, —CO—$OR^d$ or —CO—$N(R^d)_2$ group. Most preferably $R^4$ and $R^5$ are each independently hydrogen or a —CO—$OR^d$ group.

Preferably, at least one of $R^4$ and $R^5$ is a —CO—$OR^d$ group.

Preferably $R^d$ is an unsubstituted alkyl, alkenyl, aryl, arylalkyl, arylalkenyl, alkylaryl or alkenylaryl group which optionally includes one or more heteroatoms in its carbon skeleton and preferably comprises from 1 to 12 carbon atoms. More preferably $R^d$ is an unsubstituted alkyl or alkenyl group comprising from 1 to 6 carbon atoms or an unsubstituted arylalkyl group comprising from 7 to 12 carbon atoms.

In one embodiment $R^4$ is hydrogen. In another embodiment $R^5$ is not hydrogen or an isotope thereof.

In a preferred embodiment, $R^4$ is hydrogen and $R^5$ is a —CO—$OR^d$ group, wherein $R^d$ is an unsubstituted alkyl or alkenyl group comprising from 1 to 6 carbon atoms or an unsubstituted arylalkyl group comprising from 7 to 12 carbon atoms.

Preferably $R^5$ is selected from —$CO_2Et$, —$CO_2{}^iPr$, —$CO_2{}^tBu$, —$CO_2Bn$ or —$CO_2CH_2CH$=$CH_2$.

In one embodiment, any of $R^1$, $R^2$ and $R^3$ form part of the same group as any of $R^4$ and $R^5$, such that the imine (I), or a precursor thereof, and the diazo compound (II) form part of the same molecule and the reaction is intramolecular.

In another embodiment of the first aspect of the present invention, at least one of $R^6$, $R^7$, $R^8$ and $R^9$ is chiral.

In yet another embodiment, $R^6$, $R^7$, $R^8$ and $R^9$ are each independently hydrogen, halogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein any two or more of $R^6$, $R^7$, $R^8$ and $R^9$ together with the atom or atoms to which they are attached may form a cyclic hydrocarbyl group which may optionally be substituted and which may optionally include one or more heteroatoms N, O or S in its carbon skeleton.

In one embodiment $R^9$ is hydrogen, halogen or a substituted or unsubstituted alkyl, alkenyl, aryl, arylalkyl, arylalkenyl, alkylaryl or alkenylaryl group which optionally includes one or more heteroatoms in its carbon skeleton and preferably comprises from 1 to 12 carbon atoms. More preferably $R^9$ is hydrogen or an unsubstituted alkyl group comprising from 1 to 6 carbon atoms.

In another embodiment, X is O or S. Most preferably X is $O_2$.

$R^6$ may be an electron withdrawing group. In one embodiment, $R^6$ is selected from a —CO—$R^e$, —CO—$OR^e$, —CO—$N(R^e)_2$, —CS—$R^e$, —CS—$OR^e$, —CS—$N(R^e)_2$, —C=$NR^e$—$N(R^e)_2$, —C=$NR^e$—$R^e$, —C=$NR^e$—$OR^e$, —SO—$R^e$, —SO—$OR^e$, —SO—$N(R^e)_2$, —$SO_2$—$R^e$, —$SO_2$—$OR^e$, —$SO_2$'$N(R^e)_2$ or —$PO(R^e)_2$ group, wherein each —$R^e$ is independently hydrogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises from 1 to 15 carbon atoms. Preferably $R^6$ is selected from a —CO—$R^e$, —SO—$R^e$ or —$SO_2$—$R^e$ group. Most preferably $R^6$ is a —$SO_2$—$R^e$ group.

Preferably $R^e$ is a substituted or unsubstituted alkyl, alkenyl, aryl, arylalkyl, arylalkenyl, alkylaryl or alkenylaryl group which optionally includes one or more heteroatoms in its carbon skeleton and preferably comprises from 1 to 12 carbon atoms. More preferably $R^e$ is a substituted or unsubstituted alkyl or aryl group comprising from 1 to 6 carbon atoms.

Where $R^e$ is substituted, preferably it is substituted with one or more of —F, —Cl, —Br, —I, —CF$_3$, —CCl$_3$, —CBr$_3$, —CI$_3$, —OH, —SH, —NH$_2$, —N$_3$, —NH=NH$_2$, —CN, —NO$_2$, —COOH, —R$^a$—O—R$^b$, —R$^a$—S—R$^b$, —SO—R$^b$, —SO$_2$—R$^b$, —SO$_2$—OR$^b$, —O—SO$_2$—R$^b$, —O—SO$_2$—OR$^b$, —R$^a$—N(R$^b$)$_2$, —R$^a$—N(R$^b$)$_3$$^+$, —R$^a$—Si(R$^b$)$_3$, —R$^a$—CO—R$^b$, —R$^a$—CO—OR$^b$, —R$^a$O—CO—R$^b$, —R$^a$—CO—N(R$^b$)$_2$, —R$^a$—NR$^b$—CO—R$^b$, —R$^a$O—CO—OR$^b$, —R$^a$—CS—R$^b$ or —R$^b$; wherein $R^a$ and $R^b$ are as defined below. More preferably, where $R^a$ is substituted, it is substituted with one or more of —F, —Cl, —Br, —I, —CF$_3$, —CCl$_3$, —CBr$_3$ or —CI$_3$.

In a preferred embodiment of the first aspect of the present invention, $R^6$ is —SO$_2$CF$_3$.

In one embodiment of the first aspect of the present invention, $R^7$ and $R^8$ together form a bidentate ligand. Optionally said bidentate ligand is chiral. Preferably $R^7$ and $R^8$ together form a chiral bidentate ligand of formula (VI):

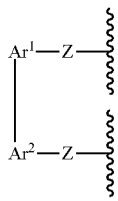

(VI)

wherein each Z is independently selected from O, S or NR$^f$, wherein each $R^f$ is independently hydrogen, halogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein Ar$^1$ and Ar$^2$ are each independently a substituted or unsubstituted arylene group which optionally includes one or more heteroatoms in its carbon skeleton.

In one embodiment, each $R^f$ is hydrogen or a hydrocarbyl group comprising from 1 to 15 carbon atoms.

Preferably each Z is independently selected from O or S. Preferably each Z is the same. Most preferably each Z is O.

In one embodiment, Ar$^1$ and Ar$^2$ are each independently selected from a substituted or unsubstituted polycyclic arylene group such as a bicyclic or tricyclic arylene group, which optionally includes one or more heteroatoms in its carbon skeleton.

Preferably Ar$^1$ and Ar$^2$ are each independently selected from a substituted or unsubstituted naphthalenylene, 1,4-dihydronaphthalenylene, tetralinylene, indenylene, indolizinylene, indolylene, isoindolylene, 3H-indolylene, indolinylene, benzofuranylene, benzothiophenylene, 1H-indazolylene, benzimidazolylene, benzthiazolylene, purinylene, 4H-quinolizinylene, quinolinylene, isoquinolinylene, cinnolinylene, phthalazinylene, quinazolinylene, quinoxalinylene, 1,8-naphthyridinylene, pteridinylene, 3-benzazepinylene, 1,4-benzodiazepinylene, anthracenylene, phenanthrenylene, carbazolylene, acridinylene, phenazinylene, phenothiaznylene, phenoxazinylene, carbolinylene, dibenzofuranylene, dibenzothiophenylene, chrysenylene, pyrenylene or tetracenylene group.

More preferably Ar$^1$ and Ar$^2$ are each independently selected from a substituted or unsubstituted naphthalenylene, 1,4-dihydronaphthalenylene or tetralinylene group. Most preferably Ar$^1$ and Ar$^2$ are each independently selected from a substituted or unsubstituted naphthalenylene group.

In one embodiment, Ar$^1$ and Ar$^2$ are both substituted. Where substituted, Ar$^1$ and Ar$^2$ may each independently be substituted with 1, 2, 3, 4, 5, 6, 7, 8 or more substituents. Preferably Ar$^1$ and Ar$^2$ are each independently substituted with 1 or 2 substituents. Most preferably Ar$^1$ and Ar$^2$ are each substituted with 1 substituent.

Where substituted, Ar$^1$ and Ar$^2$ may in one embodiment each independently be substituted with a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein any two or more hydrocarbyl groups together with the atom or atoms to which they are attached may form a cyclic hydrocarbyl group which may optionally be substituted and which may optionally include one or more heteroatoms N, O or S in its carbon skeleton.

Preferably, where substituted Ar$^1$ and Ar$^2$ are each independently substituted with a substituted or unsubstituted aryl, arylalkyl, arylalkenyl, arylalkynyl, alkylaryl, alkenylaryl or alkynylaryl group which optionally includes one or more heteroatoms in its carbon skeleton. Most preferably, where substituted Ar$^1$ and Ar$^2$ are each independently substituted with an unsubstituted aryl group.

Preferably each hydrocarbyl group used to substitute Ar$^1$ and Ar$^2$ comprises from 1 to 50 carbon atoms. More preferably each hydrocarbyl group used to substitute Ar$^1$ and Ar$^2$ comprises from 6 to 24 carbon atoms. Preferably, where a hydrocarbyl group used to substitute Ar$^1$ or Ar$^2$ is itself substituted, it is substituted with one or more of —F, —Cl, —Br, —I, —CF$_3$, —CCl$_3$, —CBr$_3$ or —CI$_3$.

In a preferred embodiment, $R^7$ and $R^8$ together form a chiral bidentate ligand of formula (VIa), (VIa') or (VIa"):

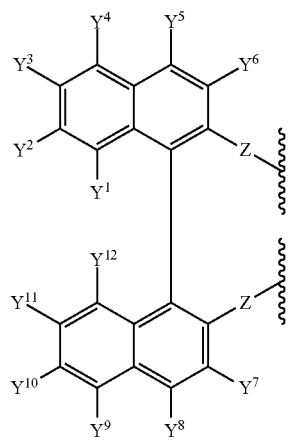

(VIa)

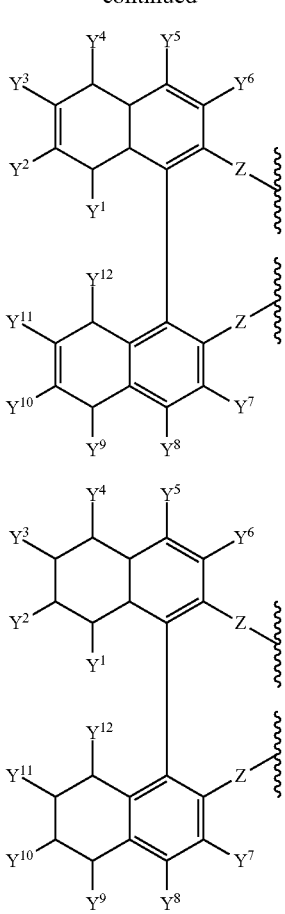

wherein Z is as defined above and wherein $Y^1$, $Y^2$, $Y^3$, $Y^4$, $Y^5$, $Y^6$, $Y^7$, $Y^8$, $Y^9$, $Y^{10}$, $Y^{11}$ and $Y^{12}$ are each independently hydrogen, halogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein any two or more or $Y^1$, $Y^2$, $Y^3$, $Y^4$, $Y^5$, $Y^6$, $Y^7$, $Y^8$, $Y^9$, $Y^{10}$, $Y^{11}$ and $Y^{12}$ together with the atom or atoms to which they are attached may form a cyclic hydrocarbyl group which may optionally be substituted and which may optionally include one or more heteroatoms N, O or S in its carbon skeleton.

Preferably, $R^7$ and $R^8$ together form a chiral bidentate ligand of formula (VIa).

In one embodiment, at least six of $Y^1$, $Y^2$, $Y^3$, $Y^4$, $Y^5$, $Y^6$, $Y^7$, $Y^8$, $Y^9$, $Y^{10}$, $Y^{11}$ and $Y^{12}$ are hydrogen. Preferably at least eight of $Y^1$, $Y^2$, $Y^3$, $Y^4$, $Y^5$, $Y^6$, $Y^7$, $Y^8$, $Y^9$, $Y^{10}$, $Y^{11}$ and $Y^{12}$ are hydrogen. Most preferably at least ten of $Y^1$, $Y^2$, $Y^3$, $Y^4$, $Y^5$, $Y^6$, $Y^7$, $Y^8$, $Y^9$, $Y^{10}$, $Y^{11}$ and $Y^{12}$ are hydrogen.

Preferably $Y^1$, $Y^2$, $Y^3$, $Y^4$, $Y^5$, $Y^8$, $Y^9$, $Y^{10}$, $Y^{11}$ and $Y^{12}$ are hydrogen and $Y^6$ and $Y^7$ are each independently hydrogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton. Preferably $Y^6$ and $Y^7$ are the same. Preferably $Y^6$ and $Y^7$ are not hydrogen.

Preferably $Y^6$ and $Y^7$ are each independently a substituted or unsubstituted aryl, arylalkyl or alkylaryl group which optionally includes one or more heteroatoms in its carbon skeleton. More preferably $Y^6$ and $Y^7$ are each independently a substituted or unsubstituted fused aryl group, such as a naphthyl, anthracenyl or phenanthrenyl group, which optionally includes one or more heteroatoms in its carbon skeleton.

Preferably $Y^6$ and $Y^7$ each comprise from 1 to 50 carbon atoms. More preferably $Y^6$ and $Y^7$ each comprise from 6 to 24 carbon atoms.

Preferably, where any of $Y^1$, $Y^2$, $Y^3$, $Y^4$, $Y^5$, $Y^6$, $Y^7$, $Y^8$, $Y^9$, $Y^{10}$, $Y^{11}$ or $Y^{12}$ are substituted, they are substituted with one or more of —F, —Cl, —Br, —I, —CF$_3$, —CCl$_3$, —CBr$_3$ or —CI$_3$.

In one embodiment of the first aspect of the present invention, $R^7$ and $R^8$ together form a chiral bidentate ligand of formula (VIb), (VIb') or (VIb"):

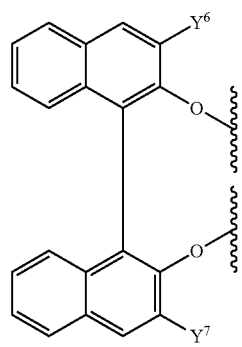

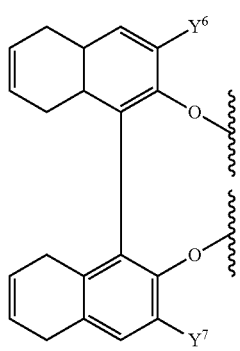

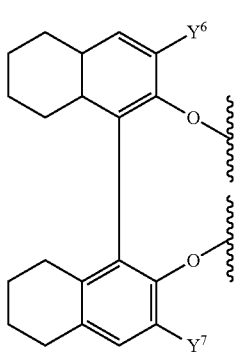

wherein $Y^6$ and $Y^7$ are the same and are selected from hydrogen.

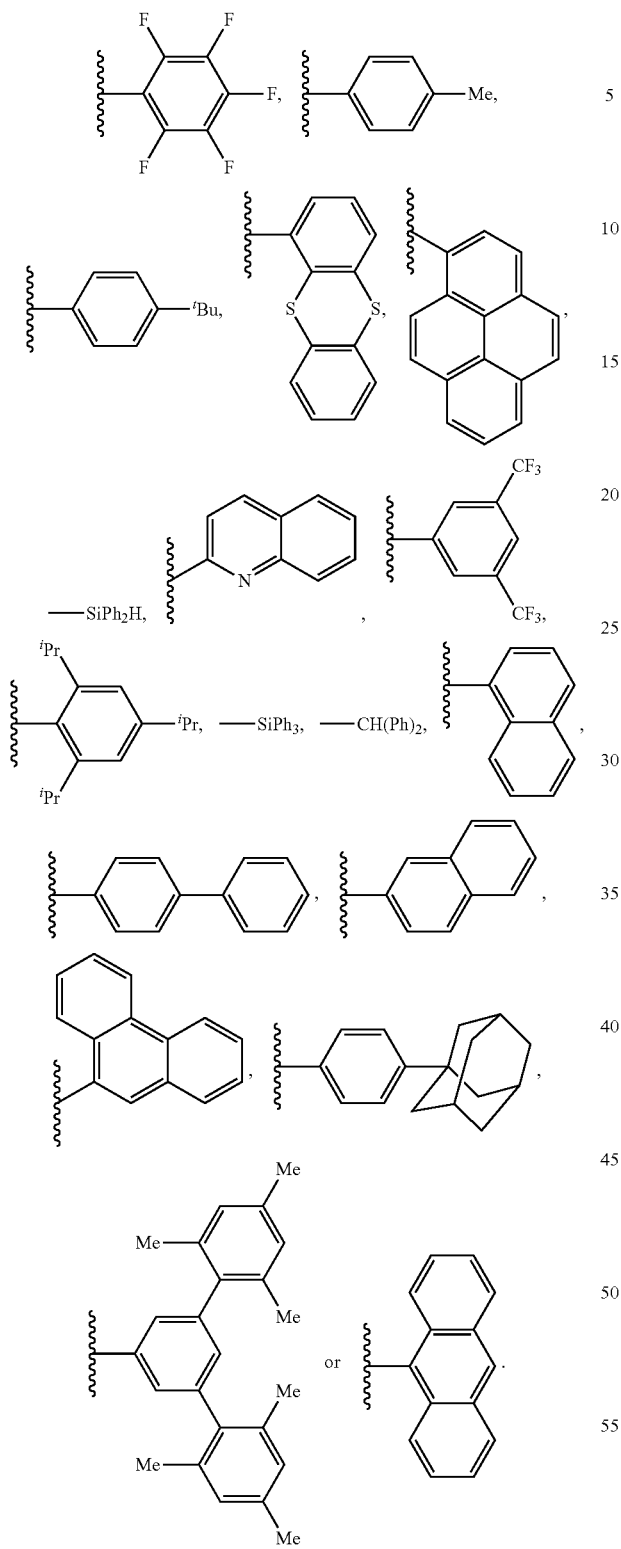

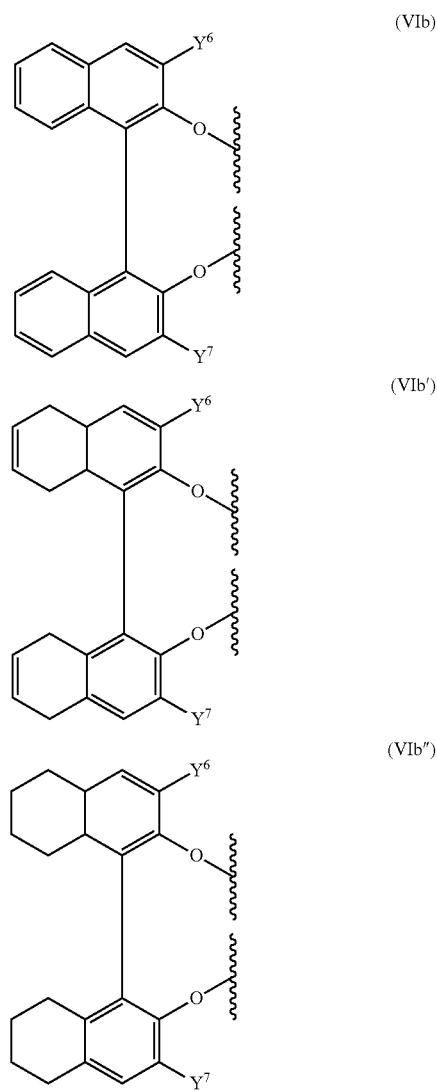

In another embodiment of the first aspect of the present invention, $R^7$ and $R^8$ together form a chiral bidentate ligand of formula (VIb), (VIb') or (VIb''):

wherein $Y^6$ and $Y^7$ are each independently selected from a substituted or unsubstituted aryl, arylalkyl or alkylaryl group which, optionally includes one or more heteroatoms in its carbon skeleton. Preferably $Y^6$ and $Y^7$ are each independently selected from a substituted or unsubstituted fused aryl group, such as a naphthyl, anthracenyl or phenanthrenyl group, which optionally includes one or more heteroatoms in its carbon skeleton. Preferably $Y^6$ and $Y^7$ are the same.

In a particularly preferred embodiment of the first aspect of the invention, the catalyst is a compound of formula (IV) or a salt thereof, wherein X is O, $R^6$ is a —$SO_2$—$R^e$ group, and $R^7$ and $R^8$ together form a chiral bidentate ligand of formula (VIb), (VIb') or (VIb'') as defined above.

Preferably $R^7$ and $R^8$ together form a chiral bidentate ligand of formula (VIb).

Most preferably, $R^7$ and $R^8$ together form a chiral bidentate ligand of formula (VIb) wherein $Y^6$ and $Y^7$ are both

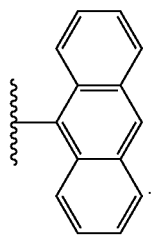 [SMILES: *c1c2ccccc2cc2ccccc12]

In a preferred embodiment, where the catalyst of formula (IV) or of formula (V) is chiral, it is present as a single enantiomer, optionally in salt form.

Alternately, where the catalyst of formula (IV) or of formula (V) is chiral, it may be present as a mixture of enantiomers, optionally in salt form. Preferably the mixture is enantiomerically enriched. Preferably the enantiomeric excess (e.e.) within such a mixture is at least 50%. More preferably the e.e. is at least 75%, at least 85%, at least 90%, or at least 95%. Most preferably the enantiomeric excess (e.e.) within such a mixture is at least 99%.

Alternately still, where the catalyst of formula (IV) or of formula (V) is chiral, it may be present as a racemic mixture.

As discussed above, in one embodiment of the first aspect of the present invention, the imine (I), one or more precursors thereof, and/or the diazo compound (II) may be isotopically labelled, preferably such that the resultant aziridine (III) is also isotopically labelled.

For example, at least one of $R^1$, $R^2$, $R^3$, $R^4$ and $R^5$ may be $^2H$ or $^3H$. Preferably at least one of $R^1$, $R^2$, $R^4$ and $R^5$ is $^2H$ or $^3H$. Most preferably $R^1$ and/or $R^4$ are $^2H$ or $^3H$.

Alternatively or in addition, any nitrogen atom within the imine (I), the one or more precursors thereof, and/or the diazo compound (II) may be $^{15}N$. For instance, any nitrogen atom within any of $R^1$, $R^2$, $R^3$, $R^4$ and/or $R^5$ may be $^{15}N$. Preferably the nitrogen atom of the C=N group of the imine (I) and/or the nitrogen atom of the amine $H_2NR^3$ or the protected derivative thereof is $^{15}N$, such that the nitrogen atom in the aziridine ring of (III) is $^{15}N$.

Similarly, any carbon atom within the imine (I), the one or more precursors thereof, and/or the diazo compound (II) may be $^{13}C$ or $^{14}C$. For instance, any carbon atom within any of $R^1$, $R^2$, $R^3$, $R^4$ and/or $R^5$ may be $^{13}C$ or $^{14}C$. Preferably the carbon atom of the C=N group of the imine (I) and/or the carbon atom of the C=O group of the carbonyl compound $R^1COR^2$ or the protected derivative thereof, and/or the carbon atom of the C=$N_2$ group of the diazo compound (II) is $^{13}C$ or $^{14}C$, such that one or both of the carbon atoms in the aziridine ring of (III) is $^{13}C$ or $^{14}C$.

Likewise, any other heteroatom within the imine (I), the one or more precursors thereof, the diazo compound (II) and/or the aziridine (III) may be isotopically labelled. For instance, any heteroatom within any of $R^1$, $R^2$, $R^3$, $R^4$ and/or $R^5$ may be isotopically labelled. Typically, any oxygen atom may be $^{18}O$; any fluorine atom may be $^{18}F$; any iodine atom may be $^{123}I$, $^{125}I$ or $^{131}I$; and/or any phosphorous atom may be $^{33}P$ or $^{34}P$.

In one embodiment of the first aspect of the present invention, $R^1$ and $R^4$ in the aziridine (III) are mostly cis- or mostly trans-.

Where $R^1$ and $R^4$ are mostly trans-, preferably at least 60 mol % of the aziridine (III) is the cis-isomer. More preferably, at least 70 mol %, at least 80 mol %, at least 90 mol %, at least 95 mol % or at least 99 mol % of the aziridine (III) is the cis-isomer. Most preferably only the cis-isomer is synthesised.

Alternately, where $R^1$ and $R^4$ are mostly trans-, preferably at least 60 mol % of the aziridine (III) is the trans-isomer. More preferably, at least 70 mol %, at least 80 mol %, at least 90 mol %, at least 95 mol % or at least 99 mol % of the aziridine (III) is the trans-isomer. Most preferably only the trans-isomer is synthesised.

In yet another embodiment of the first aspect of the present invention, the synthesis of the aziridine (III) is enantioselective. Preferably an enantiomer of the aziridine (III) is synthesised with an e.e. of at least 50%. More preferably an enantiomer of the aziridine (III) is synthesised with an e.e. of at least 75%, at least 85%, at least 90%, or at least 95%. Most preferably an enantiomer of the aziridine (III) is synthesised with an e.e. of at least 99%.

Typically, the aziridine (III) is synthesised in a molar yield of at least 75% from the imine (I) or the salt or one or more precursors thereof. Preferably, the aziridine (III) is synthesised in a molar yield of at least 80%, at least 85% or at least 90%. Most preferably, the aziridine (III) is synthesised in a molar yield of at least 95%.

In one embodiment of the first aspect of the present invention, the imine (I) or the salt or the one or more precursors thereof are contacted with the diazo compound (II) or the salt thereof in an organic solvent selected from a non-polar solvent or a dipolar aprotic solvent, or a mixture thereof. Preferably the organic solvent is a non-polar solvent. Exemplary non-polar solvents include alkanes and cycloalkanes such as n-hexane, cyclohexane or n-heptane, aromatic hydrocarbons such as toluene or benzene, alkyl ethers and cycloalkyl ethers such as diethyl ether, tert-butyl methyl ether, tetrahydrofuran (THF) or 1,4-dioxane, and halocarbons including chlorohydrocarbons such as chloroform or dichloromethane (DCM). Preferably the non-polar solvent is a chlorohydrocarbon, most preferably chloroform or dichloromethane.

In a further embodiment, the imine (I) or the salt or the one or more precursors thereof are contacted with the diazo compound (II) or the salt thereof in a solvent comprising a mixture of halocarbons. Preferably the mixture of halocarbons is a mixture of halohydrocarbons and/or a mixture of chlorocarbons. More preferably, the mixture of halocarbons is a mixture of chlorohydrocarbons such as a mixture of chloroform and dichloromethane.

The above embodiment is preferred when the imine (I), one or more precursors thereof, and/or the diazo compound (II) are isotopically labelled, and is particularly preferred when at least one of $R^1$, $R^2$, $R^3$, $R^4$ and $R^5$ is $^3H$ or $^5H$. Optionally one or more of the halohydrocarbons such as the chlorohydrocarbons may be labelled with $^2H$ or $^3H$; for example deuterated chloroform and/or deuterated dichloromethane may be used.

Where a solvent comprising a mixture of halocarbons is used, it is preferred that the catalyst is a chiral compound of formula (IV) or a salt thereof, wherein X is O. More preferably, the catalyst is a chiral compound of formula (IV) or a salt thereof, wherein X is O, wherein $R^6$ is a —$SO_2$—$R^e$ group, and wherein $R^7$ and $R^8$ together form a chiral bidentate ligand of formula (VIb), (VIb') or (VIb''), wherein $Y^6$ and $Y^7$ are each independently selected from a substituted or unsubstituted aryl, arylalkyl or alkylaryl group which optionally includes one or more heteroatoms in its carbon skeleton. More preferably still $Y^6$ and $Y^7$ are each independently selected from a substituted or unsubstituted fused aryl group, such as a naphthyl, anthracenyl or phenanthrenyl group, which optionally includes one or more heteroatoms in its carbon skeleton. Preferably $Y^6$ and $Y^7$ are the same.

Most preferably, where a solvent comprising a mixture of halocarbons is used, the catalyst is a chiral compound of formula (IV) or a salt thereof, wherein X is O, wherein $R^6$ is —$SO_2CF_3$, and wherein $R^7$ and $R^8$ together form a chiral bidentate ligand of formula (VIb) wherein $Y^6$ and $Y^7$ are both

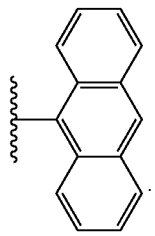 [SMILES: *c1c2ccccc2cc2ccccc12]

In a particularly preferred embodiment of the first aspect of the present invention, the imine (I) or the salt or the one or more precursors thereof are contacted with the diazo compound (II) or the salt thereof in a solvent comprising a mixture of halocarbons; the imine (I), one or more precursors thereof, and/or the diazo compound (II) are isotopically labelled such that the resultant aziridine (III) is also isotopically labelled; and the catalyst is a chiral compound of formula (IV) wherein X is O and preferably wherein $R^6$ is —$SO_2CF_3$ and $R^7$ and $R^8$ together form a chiral bidentate ligand of formula (VIb) wherein $Y^6$ and $Y^7$ are both

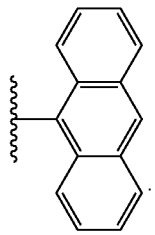 [SMILES: *c1c2ccccc2cc2ccccc12]

Preferably, wherein the imine (I) or the salt or the one or more precursors thereof are contacted with the diazo compound (II) or the salt thereof in a mixture of chloroform and dichloromethane, the ratio of chloroform:dichloromethane in the mixture is from 50:50 to 95:5 by volume. More preferably, the ratio of chloroform:dichloromethane in the mixture is from 70:30 to 90:10 by volume. Most preferably, the ratio of chloroform:dichloromethane in the mixture is about 80:20 by volume.

Optionally the organic solvent may be dried prior to use, for example over molecular sieves.

In another embodiment of the first aspect of the present invention, the imine (I) or the salt or the one or more precursors thereof are contacted with the diazo compound (II) or the salt thereof at a temperature of from −150° C. to 50° C. Preferably the temperature is from −125° C. to 0° C., more preferably from −100° C. to −50° C., more preferably still from −90 to −65° C., and most preferably from −85 to −75° C.

Typically, the catalyst is added at a concentration of from 0.01 to 25 mol %, relative to the imine (I) or the salt or the one or more precursors thereof. Preferably, the catalyst is added at a concentration of from 0.1 to 15 mol %, more preferably at a concentration of from 0.5 to 5 mol %, and most preferably at a concentration of about 1 mol %.

Typically, from 0.2 to 5 equivalents of the diazo compound (II) or the salt thereof are used relative to the imine (I) or the salt or the one or more precursors thereof.

Preferably from 0.5 to 2 equivalents of the diazo compound (II) or the salt thereof are used, more preferably from 0.65 to 1.5 equivalents are used, and most preferably about 1.1 equivalents of the diazo compound (II) or the salt thereof are used.

The catalyst may be contacted with the imine (I) or the salt or the one or more precursors thereof before, after or simultaneously with the addition of the diazo compound (II) or the salt thereof. Preferably the catalyst is contacted with the imine (I) or the salt or the one or more precursors thereof before the addition of the diazo compound (II) or the salt thereof.

Typically, the diazo compound (II) or the salt thereof is allowed to react with the imine (I) or the salt or the one or more precursors thereof for a period of from 30 minutes to 2 weeks. Preferably, the diazo compound (II) or the salt thereof is allowed to react with the imine (I) or the salt or the one or more precursors thereof for a period of from 1 hour to 1 week. More preferably, the diazo compound (II) or the salt thereof is allowed to react with the imine (I) or the salt or the one or more precursors thereof for a period of from 12 hours to 96 hours, more preferably still for a period of from 24 hours to 72 hours.

Optionally, the reaction may occur under an inert atmosphere such as nitrogen or argon.

In another embodiment, the method further comprises the step of synthesising the diazo compound (II). Techniques for the synthesis of diazo compounds such as (II) are known in the art; see for example page 495 of "Advanced Organic Chemistry" by J. March (John Wiley & Sons, 4th Edition, 1992).

In yet another embodiment, the method further comprises the steps of:
(a) chemically modifying or cleaving any of $R^1$, $R^2$, $R^3$, $R^4$ or $R^5$ to give a modified aziridine or a salt thereof; and/or
(b) ring-opening or ring-expanding the aziridine (III) or the modified aziridine to give an aziridine-derived compound or a salt thereof.

The aziridine-derived compound may for instance comprise one or more of the following structural groups:

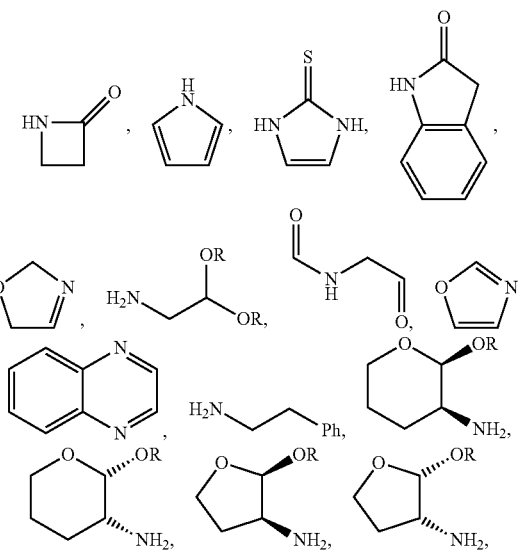

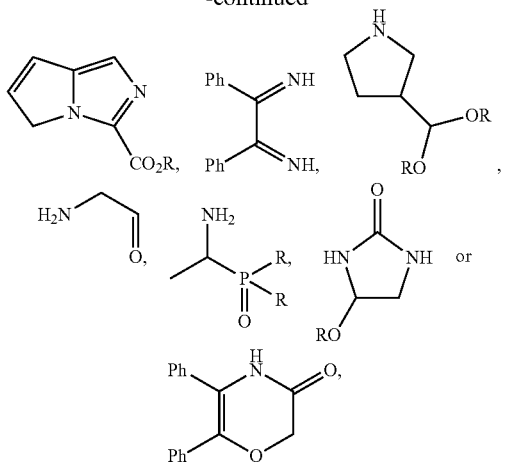

wherein R represents any atom or group and is preferably alkyl, and wherein any hydrogen may be replaced by any atom or group. Optionally one or more hydrogen atoms in the structural groups are replaced by one or more or $R^1$, $R^2$, $R^3$, $R^4$ and $R^5$. Preferably one or more hydrogen atoms bonded to a carbon atom in the structural groups are replaced by one or more of $R^1$, $R^2$, $R^4$ and $R^5$. Preferably one or more hydrogen atoms bonded to a nitrogen atom in the structural groups are replaced by $R^3$.

Optionally, the aziridine-derived compound is isotopically labelled, for example with $^2H$ or $^3H$. Typically, where the aziridine-derived compound is isotopically labelled, the aziridine-derived compound is derived from an istotopically labelled aziridine (III). Examples of isotopic labelling of the aziridine (III) are described above.

Optionally, the aziridine-derived compound may be a synthetic equivalent of a natural product.

Alternatively or in addition, the aziridine-derived compound may be an α- or β-amino acid, a chiral auxiliary, a polymer, an azasugar, or a heterocyclic entity such as an oxazolidinone, imidazolidine, β-lactam, thioxazolidinethione or pyrrolidine.

In another embodiment of the first aspect of the invention, the aziridine (III) or the modified aziridine may be selected from the Azinomycins, Ficellomycin, Miraziridine, Maduropeptin, PBI-A, Mitomycin A, FR66979 and NSC 639823.

A second aspect of the present invention relates to an aziridine or a salt thereof, or a modified aziridine or a salt thereof or an aziridine-derived compound or a salt thereof, preparable by a method according to the first aspect of the present invention. Optionally, said aziridine or salt thereof, or modified aziridine or salt thereof, or aziridine-derived compound or salt thereof is isotopically labelled, preferably as described in relation to the first aspect of the present invention.

A third aspect of the present invention relates to an isotopically labelled aziridine or a salt thereof, wherein the isotopically labelled aziridine is not a meso compound, but would be a meso compound if it were not isotopically labelled.

In one embodiment of the third aspect of the present invention, the isotopically labelled aziridine is a compound of formula (IIIa):

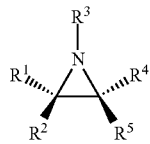

wherein $R^1$, $R^2$, $R^3$, $R^4$ and $R^5$ are as defined in relation to any embodiment of the first aspect of the present invention, and wherein one or more of $R^1$, $R^2$, $R^4$ and $R^5$ and the carbon atoms of the aziridine ring are isotopically labelled.

Preferably, $R^1$ and $R^4$ are different and are selected from $^1H$, $^2H$ and $^3H$ $R^2$ and $R^5$ are the same and are selected from any atom or group other than hydrogen; and $R^3$ is independently selected from any atom or group.

For instance, $R^2$ and $R^5$ may both be she same —CO—$OR^d$ group, wherein $R^d$ is as defined above. $R^3$ is preferably a substituted or unsubstituted alkyl, alkenyl, aryl, arylalkyl or alkylaryl group which optionally includes one or more heteroatoms in its carbon skeleton. More preferred examples of $R^3$ are as defined above in relation to the first aspect of the present invention.

Examples of isotopically labelled aziridines according to the third aspect of the present invention include stereochemically pure compounds of formulae 22 and 23 below:

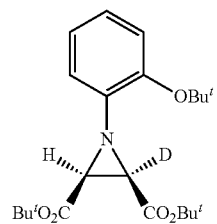

22

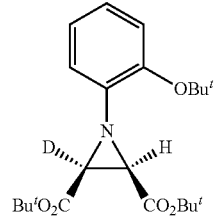

23

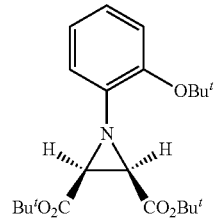

24

It can be seen that due to the isotopic labelling with deuterium, compounds 22 and 23 are non-superimposable mirror images of each other, i.e. they are enantiomers not meso compounds. If compounds 22 and 23 were not isotopically labelled however, they would both be the same compound, the meso compound 24.

In a preferred embodiment of the third aspect of the present invention, the isotopically labelled aziridine or the salt thereof has a stereochemical purity of ≥75%. More preferably, the stereochemical purity is ≥80%, ≥90% or ≥95%. More preferably still, the stereochemical purity is ≥98% or ≥99%. Most preferably, the stereochemical purity is ≥99.5%.

As will be appreciated, techniques such as the measurement of optical rotation or the use of chiral HPLC will not allow the full analysis of the stereochemical purity of the compounds of the third aspect of the present invention, since such techniques are unable to differentiate between compounds such as 22 and 23. Instead, other analytical techniques known to the skilled person must be used.

For example, vibrational circular dichroism (VCD) in conjunction with computer modelling may be used to elucidate the absolute configuration of the isotopically labelled aziridine. Such techniques are reported in studies by Freedman et al. (Journal of the American Chemical Society, 1987, vol. 109, pp. 4727-8) and Lin et al. (Physical Chemistry Chemical Physics, 2012, vol. 14, pp. 3669-3680).

Alternatively, the isotopically labelled aziridine may be chemically modified using a chiral auxiliary, for example by ring-opening the aziridine or by the reaction of a substituent group, e.g. by transesterification in the case of an ester substituent. The resultant chemically modified aziridine may then be analysed, for example using NMR techniques, to determine the stereochemical purity of the initial isotopically labelled aziridine. Such a technique is also reported in the article by Freedman et al. (see footnote 15).

A fourth aspect of the present invention relates to an isotopically labelled modified aziridine or a salt thereof or an isotopically labelled aziridine-derived compound or a salt thereof, preparable by chemically modifying, ring-opening or ring-expanding the isotopically labelled aziridine or the salt thereof of the third aspect of the present invention. Such chemical modifications, ring-openings and ring-expansions, and the resultant modified aziridines and aziridine-derived compounds may be as described above in relation to the first aspect of the present invention.

A fifth aspect of the present invention relates to a compound of formula (IV) or a salt thereof, or a compound of formula (V) or a salt thereof:

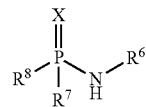

(IV)

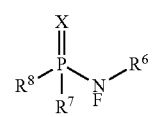

(V)

wherein X is O, S or NR$^9$, and R$^6$, R$^7$, R$^8$ and R$^9$ each independently represent any atom or group, with the proviso that when X is O, R$^6$ is —SO$_2$CF$_3$, and R$^7$ and R$^8$ together form a chiral bidentate ligand of formula (VIb):

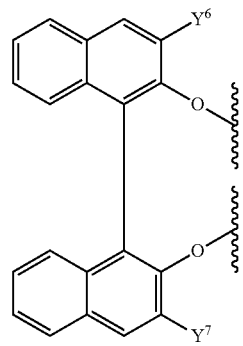

wherein Y$^6$ and Y$^7$ are the same and are selected from hydrogen,

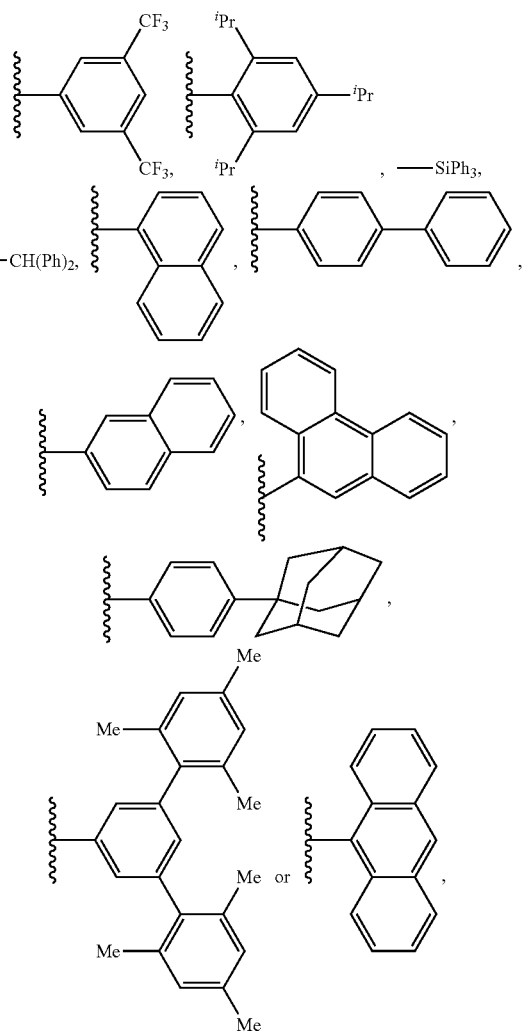

the compound is not a compound of formula (IV) or a salt thereof.

In one embodiment of the fifth aspect of the present invention, the compound of formula (IV) or (V) is chiral.

X, R$^6$, R$^7$, R$^8$ and R$^9$ may each be independently defined according to any embodiment of the first aspect of the present invention.

Optionally X is S or NR$^9$.

In one embodiment of the fifth aspect of the present invention, $R^6$ is not —$SO_2CF_3$. Optionally $R^6$ is not a —$SO_2$—$R^e$ group.

In another embodiment of the fifth aspect of the present invention, $R^7$ and $R^8$ do not together form a chiral bidentate ligand of formula (VIb) as defined above. Optionally $R^7$ and $R^8$ do not together form a chiral bidentate ligand of formula (VIa) as defined above. Optionally still, $R^7$ and $R^8$ do not together form a chiral bidentate ligand of formula (VI) as defined above.

In yet another embodiment of the fifth aspect of the present invention, $R^7$ and $R^8$ together form a chiral bidentate ligand of formula (VI):

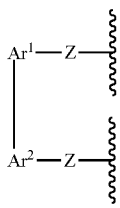

(VI)

wherein each Z is independently selected from O, S or $NR^f$, wherein each $R^f$ is independently hydrogen, halogen or a hydrocarbyl group, wherein each hydrocarbyl group independently is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein $Ar^1$ and $Ar^2$ are each independently arylene groups which optionally include one or more heteroatoms in their carbon skeleton and which are substituted with a heterocyclic aryl group.

Preferably $R^7$ and $R^8$ together form a chiral bidentate ligand of formula (VIb), (VIb') or (VIb"):

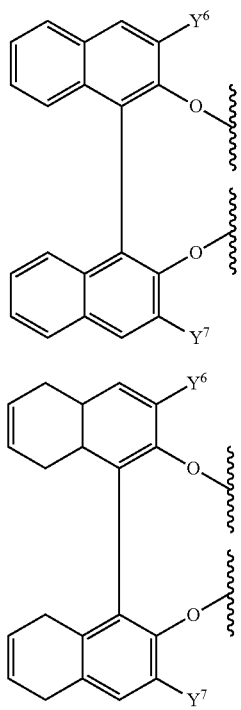

(VIb)

(VIb')

(VIb")

wherein $Y^6$ and $Y^7$ are the same and are heterocyclic aryl groups. The heterocyclic aryl groups may themselves be substituted or unsubstituted. Preferably the heterocyclic aryl groups are selected from:

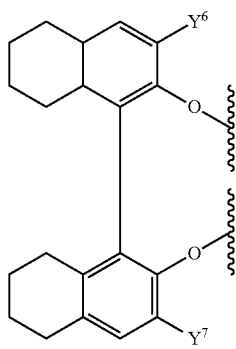

or

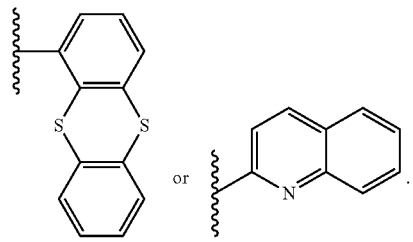

Most preferably $R^7$ and $R^8$ together form a chiral bidentate ligand of formula (VIb).

In one embodiment of the fifth aspect of the present invention the compound is a compound of formula (V) or a salt thereof. In another embodiment the compound is a compound of formula (IV) or a salt thereof.

In one embodiment of the fifth aspect of the present invention, the compound of formula (IV) or the compound of formula (V) is attached to a solid support. For example, the solid support may be a polymeric resin such as polystyrene resin, a Wang resin, a Tentagel™ resin, a metal organic, framework (MOF), an inorganic support such as silica, mesoporous silica or clays such as montmorillonite, or a dendrimer. Preferably the solid support is a polymeric resin such as polystyrene resin. Optionally, where the compound of formula (IV) is attached to a solid support, it may be any compound of formula (IV) as defined according to the first aspect of the present invention, including those excluded by the proviso of the fifth aspect of the present invention.

In a preferred embodiment of the fifth aspect of the present invention, where the compound of formula (IV) or of formula (V) is chiral, it is present as a single enantiomer, optionally in salt form.

Alternately, where the compound of formula (IV) or of formula (V) is chiral, it may be present as a mixture of enantiomers, optionally in salt form. Preferably the mixture is enantiomerically enriched. Preferably the enantiomeric excess (e.e.) within such a mixture is at least 50%. More preferably the e.e. is at least 75%, at least 85%, at least 90%, or at least 95%. Most preferably the enantiomeric excess (e.e.) within such a mixture is at least 99%.

Alternately still, where the compound of formula (IV) or of formula (V) is chiral, it may be present as a racemic mixture.

In another preferred embodiment of the fifth aspect of the present invention, X is O, R⁶ is —SO₂CF₃ and R⁷ and R⁸ together form a chiral bidentate ligand of formula (VIb):

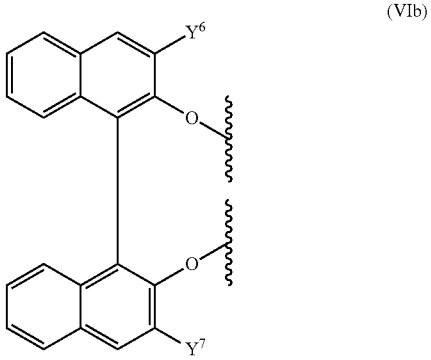

(VIb)

wherein $Y^6$ and $Y^7$ are the same and are selected from:

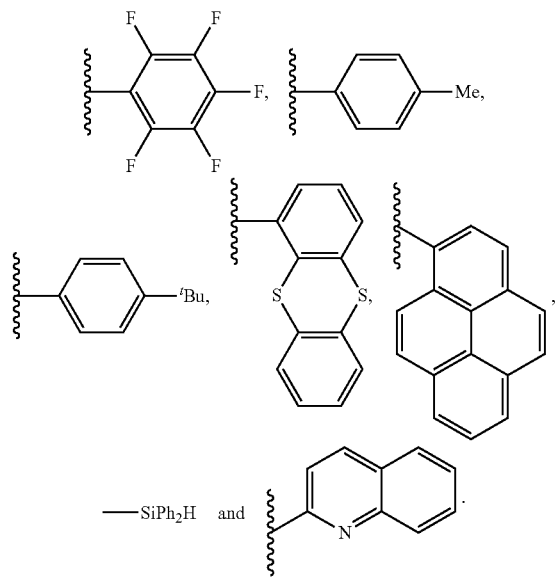

A sixth aspect of the present invention relates to the use of a compound of formula (IV) or a salt thereof, or a compound of formula (V) or a salt thereof:

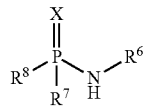

(IV)

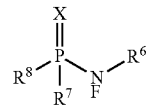

(V)

wherein X is is O, S or NR⁹, and R⁶, R⁷, R⁸ and R⁹ each independently represent any atom or group, in a method according to the first aspect of the present invention.

Optionally the compound of formula (IV) or (V) or any salt thereof as used in the sixth aspect of the present invention may be any compound of formula (IV) or (V) or any salt thereof as defined above in relation to the first or fifth aspects of the present invention.

For the avoidance of doubt, insofar as is practicable any embodiment of a given aspect of the present invention may occur in combination with any other embodiment of the same aspect of the present invention. In addition, insofar as is practicable it is to be understood that any preferred or optional embodiment of any aspect of the present invention should also be considered as a preferred or optional embodiment of any other aspect of the present invention.

Definitions

The compounds of the present invention can be used both, in their free base form and their acid addition salt form. For the purposes of this invention, a "salt" of a compound of the present invention includes an acid addition salt. Acid addition salts are preferably pharmaceutically acceptable, non-toxic addition salts with suitable acids, including but not limited to inorganic acids such as hydrohalogenic acids (for example, hydrofluoric, hydrochloric, hydrobromic or hydroiodic acid) or other inorganic acids (for example, nitric, perchloric, sulphuric or phosphoric acid); or organic acids such as organic carboxylic acids (for example, propionic, butyric, glycolic, lactic, mandelic, citric, acetic, benzoic, salicylic, succinic, malic or hydroxysuccinic, tartaric, fumaric, maleic, hydroxymaleic, mucic or galactaric, gluconic, pantothenic or pamoic acid), organic sulphonic acids (for example, methanesulphonic, trifluoromethanesulphonic, ethanesulphonic, 2-hydroxyethanesulphonic, benzenesulphonic, toluene-p-sulphonic, naphthalene-2-sulphonic or camphorsulphonic acid) or amino acids (for example, ornithinic, glutamic or aspartic acid. The acid addition salt may be a mono-, di-, tri- or multi-acid addition salt. A preferred salt is a hydrohalogenic, sulphuric, phosphoric or organic acid addition salt. A more preferred salt is a hydrochloric acid addition salt.

In addition to pharmaceutically acceptable acid addition salts, other acid addition salts are included in the present invention, since they have potential to serve as intermediates in the purification or preparation of other, for example, pharmaceutically acceptable, acid addition salts, or are useful for identification, characterisation or purification of the free base.

The compounds of the present invention can also be used both, in their free acid form and their salt form. For the purposes of this invention, a "salt" of a compound of the present invention includes one formed between a protic acid functionality (such as a carboxylic acid group) of a compound of the present invention and a suitable cation. Suitable cations include, but are not limited to lithium, sodium, potassium, magnesium, calcium and ammonium. The salt may be a mono-, di-, tri- or multi-salt. Preferably the salt is a mono- or di-lithium, sodium, potassium, magnesium, calcium or ammonium salt. More preferably the salt is a mono- or di-sodium salt. Preferably the salt is a pharmaceutically acceptable salt.

As used herein, a halogen may be —F, —Cl, —Br or —I. Preferred halogens are —F, —Cl and —Br, most preferably —F and —Cl.

For the purposes of the present invention, an "alkyl" group is defined as a monovalent saturated hydrocarbon, which may be straight-chained or branched, or be or include cyclic groups. An alkyl group may optionally include one or more heteroatoms N, O or S in its carbon skeleton. Examples of alkyl groups are methyl, ethyl, n-propyl, i-propyl, n-butyl, i-butyl, t-butyl and n-pentyl groups. Preferably an alkyl group is straight-chained or branched and does not include any heteroatoms in its carbon skeleton. Preferably an alkyl group is a $C_1$-$C_{12}$ alkyl group, which is defined as an alkyl group containing from 1 to 12 carbon atoms. More preferably an alkyl group is a $C_1$-$C_6$ alkyl group, which is defined as an alkyl group containing from 1 to 6 carbon atoms. An "alkylene" group is similarly defined as a divalent alkyl group.

An "alkenyl" group is defined as a monovalent hydrocarbon, which comprises at least one carbon-carbon double bond, which may be straight-chained or branched, or be or include cyclic groups. An alkenyl group may optionally include one or more heteroatoms N, O or S in its carbon skeleton. Examples of alkenyl groups are vinyl, allyl, but-1-enyl and but-2-enyl groups. Preferably an alkenyl group is straight-chained or branched and does not include any heteroatoms in its carbon skeleton. Preferably an alkenyl group is a $C_2$-$C_{12}$ alkenyl group, which is defined as an alkenyl group containing from 2 to 12 carbon atoms. More preferably an alkenyl group is a $C_2$-$C_6$ alkenyl group, which is defined as an alkenyl group containing from 2 to 6 carbon atoms. An "alkenylene" group is similarly defined as a divalent alkenyl group.

An "alkynyl" group is defined as a monovalent hydrocarbon, which comprises at least one carbon-carbon triple bond, which may be straight-chained or branched, or be or include cyclic groups. An alkynyl group may optionally include one or more heteroatoms N, O or S in its carbon skeleton. Examples of alkynyl groups are ethynyl, propargyl, but-1-ynyl and but-2-ynyl groups. Preferably an alkynyl group is straight-chained or branched and does not include any heteroatoms in its carbon skeleton. Preferably an alkynyl group is a $C_2$-$C_{12}$ alkynyl group, which is defined as an alkynyl group containing from 2 to 12 carbon atoms. More preferably an alkynyl group is a $C_2$-$C_6$ alkynyl group, which is defined as an alkynyl group containing from 2 to 6 carbon atoms. An "alkynylene" group is similarly defined as a divalent alkynyl group.

An "aryl" group is defined as a monovalent aromatic hydrocarbon. An aryl group may optionally include one or more heteroatoms N, O or S in its carbon skeleton. Examples of aryl groups are phenyl, naphthyl, anthracenyl and phenanthrenyl groups. Preferably an aryl group does not include any heteroatoms in its carbon skeleton. Preferably an aryl group is a $C_4$-$C_{14}$ aryl group, which is defined as an aryl group containing from 4 to 14 carbon atoms. More preferably an aryl group is a $C_6$-$C_{10}$ aryl group, which is defined as an aryl group containing from 6 to 10 carbon atoms. An "arylene" group is similarly defined as a divalent aryl group.

An "acyl" group is defined as a —CO-alkyl, —CO-alkenyl, —CO-alkynyl, —CO-aryl, —CO-arylalkyl, —CO-arylalkenyl, —CO-arylalkynyl, —CO-alkylaryl, —CO-alkenylaryl or —CO-alkynylaryl group.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

A substituted hydrocarbyl group such as a substituted alkyl, alkenyl, alkynyl, acyl, aryl, arylalkyl, arylalkenyl, arylalkynyl, alkylaryl, alkenylaryl or alkynylaryl group may be substituted with one or more of —F, —Cl, —Br, —I, —CF$_3$, —CCl$_3$, —CBr$_3$, —CI$_3$, —OH, —SH, —NH$_2$, —N$_3$, —NH=NH$_2$, —CN, —NO$_2$, —COOH, —R$^a$—O—R$^b$, —R$^a$—S—R$^b$, —R$^a$—SO—R$^b$, —R$^a$—SO$_2$—R$^b$, —R$^a$—SO$_2$—OR$^b$, —R$^a$O—SO$_2$—R$^b$, —R$^a$—SO$_2$—N(R$^b$)$_2$, —R$^a$—NR$^b$—SO$_2$—R$^b$, —R$^a$O—SO$_2$—OR$^b$, —R$^a$O—SO$_2$—N(R$^b$)$_2$, —R$^a$—NR$^b$—SO$_2$—OR$^b$, —R$^a$—NR$^b$—SO$_2$—N(R$^b$)$_2$, —R$^a$—N(R$^b$)$_2$, —R$^a$—N(R$^b$)$_3$$^+$, —R$^a$—B(R$^b$)$_2$, —R$^a$—P(R$^b$)$_2$, —R$^a$—PO(R$^b$)$_2$, —R$^a$—Si(R$^b$)$_3$, —R$^a$—CO—R$^b$, —R$^a$—CO—OR$^b$, —R$^a$O—CO—R$^b$, —R$^a$—CO—N(R$^b$)$_2$, —R$^a$—NR$^b$—CO—R$^b$, —R$^a$O—CO—OR$^b$, —R$^a$O—CO—N(R$^b$)$_2$, —R$^a$—NR$^b$—CO—OR$^b$, —R$^a$—NR$^b$—CO—N(R$^b$)$_2$, —R$^a$—CS—R$^b$, —R$^a$—CS—OR$^b$, —R$^a$O—CS—R$^b$, —R$^a$—CS—N(R$^b$)$_2$, —R$^a$—NR$^b$—CS—R$^b$, —R$^a$O—CS—OR$^b$, —R$^a$O—CS—N(R$^b$)$_2$, —R$^a$—NR$^b$—CS—OR$^b$, —R$^a$—NR$^b$—CS—N(R$^b$)$_2$, —R$^b$, a bridging substituent such as —O—, —S—, —NR$^b$— or —R$^a$—, or a π-bonded substituent such as =O, =S or =NR$^b$;

wherein each —R$^a$, is independently a chemical bond, or a substituted or unsubstituted alkylene, alkenylene or alkynylene group which optionally includes one or more heteroatoms in its carbon skeleton and preferably comprises from 1 to 10 carbon atoms; and each —R$^b$ is independently hydrogen, or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton and preferably comprises from 1 to 15 carbon atoms.

Optional substituent(s) are preferably taken into account when calculating the total number of carbon atoms in the parent group substituted with the optional substituent(s). Preferably an optionally substituted hydrocarbyl group is not substituted with a bridging substituent. Preferably an optionally substituted hydrocarbyl group is not substituted with π-bonded substituent. Preferably a substituted group comprises 1, 2 or 3 substituents, more preferably 1 or 2 substituents, and even more preferably 1 substituent.

Any optional substituent may be protected. Suitable protecting groups for protecting optional substituents are known in the art, for example from "Protective Groups in Organic Synthesis" by T. W. Greene and P. G. M. Wuts (Wiley-Interscience, 4$^{th}$ edition, 2006).

Where any group comprises one or more heteroatoms in its carbon skeleton, preferably said heteroatoms are selected from B, N, O, Si, P or S. More preferably said heteroatoms are selected from N, O, Si or S. Most preferably said heteroatoms are selected from N, O or S.

For the purposes of the present invention, a "halocarbon" is any compound comprising a carbon and a halogen atom. Similarly, a "halohydrocarbon" is any compound comprising a carbon, a hydrogen and a halogen atom. A "chlorocarbon" is any compound comprising a carbon and a chlorine atom, such as carbon tetrachloride, dichloromethane and chloroform. A "chlorohydrocarbon" is any compound comprising a carbon, a hydrogen and a chlorine atom, such as dichloromethane and chloroform.

As used herein, an "electron withdrawing group" refers to any atom or group that draws electrons to itself more than a hydrogen atom would if it occupied the same position in the molecule, such as a halogen, —NO$_2$, nitrile or acyl group.

Similarly, an "electron donating group" refers to any atom or group that repels electrons from itself more than a hydrogen atom would if it occupied the same position in the molecule, such as an unsubstituted alkyl or arylalkyl group.

Unless stated otherwise, any atom specified herein may also be an isotope of said atom. For example, the term "hydrogen" encompasses $^1$H, $^2$H and $^3$H. Similarly carbon atoms are to be understood to include $^{12}$C, $^{13}$C and $^{14}$C, nitrogen atoms are to be understood to include $^{14}$N and $^{15}$N, oxygen atoms are to be understood to include $^{16}$O, $^{17}$O and $^{18}$O, phosphorous atoms are to be understood to include $^{31}$P, $^{32}$P and 33P, iodine atoms are to be understood to include $^{123}$I, $^{124}$I, $^{125}$I, $^{127}$I and $^{131}$I, and so on.

As used herein, an "isotopically labelled" compound is one in which the abundance of a particular nuclide within the molecule is increased above the level at which it occurs in nature.

Preferably in such a compound the abundance of a particular nuclide at a particular atomic position within the molecule is increased above the level at which it occurs in nature. Accordingly, where it is stated that a particular atom is a particular nuclide, for example where it is stated that "R$^1$ is $^2$H", it is to be understood that the abundance of that particular nuclide at that atomic position is increased above the level at which it would occur in nature. Preferably the abundance is increased to at least 10%, at least 25%, at least 50%, at least 75%, at least 90% or at least 95%. Most preferably the abundance is increased to at least 90% or at least 95%.

Preferably the particular nuclide is not the naturally most abundant nuclide of a particular element. More preferably the particular nuclide is an isotopically stable nuclide such as $^2$H, $^{13}$N, $^{18}$O or $^{13}$C. Alternatively the particular nuclide may be an isotopically unstable nuclide such as $^3$H or $^{11}$C. Most preferably the particular nuclide is $^2$H.

The "stereochemical purity" of a compound refers to the molar percentage of a stereoisomer of a specific configuration within the analysed sample. For the avoidance of doubt, where a compound is isotopically labelled, the connectivity of the nuclides is taken into consideration in determining the stereochemical purity. For example, a mixture of compounds 22, 23 and 24 above, comprising 80% of 22, 10% of 23 and 10% of 24 would have a stereochemical purity, with respect to 22, of 80%.

EXAMPLES

Example 1

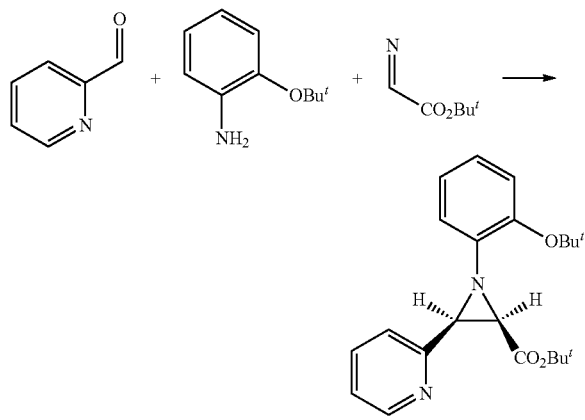

Pyridine-2-carboxaldehyde (25 µL, 0.26 mmol), o-tert-butoxy aniline (43 mg, 0.26 mmol), and catalyst (S)-3,3'-bis(9-anthracenyl)-[1,1']-binaphthalen-2,2'-yl-N-triflyl-phosphoramide (2.2 mg, 0.0026 mmol, 1 mol %) were added to a flame dried biotage 2 mL microwave vial under nitrogen, 1 mL of chloroform was added (pre-dried over 4 Å molecular sieves), followed by ~40 mg of powdered 4 Å molecular sieves, and the vial was sealed with a PTFE crimp cap. After stirring at room temperature for 6 hours, the reaction mixture was cooled to −60° C. After 30 minutes, tert-butyl diazoacetate (40 µL, 0.286 mmol) was added via syringe, and the reaction mixture was stirred at −60° C., monitoring by $^1$H-NMR until the reaction was deemed complete (~24 hours). At this point the reaction mixture was passed through a short plug of silica, eluted with diethyl ether. The solvents were removed under reduced pressure, and the residue was purified by flash chromatography (14% diethyl ether in PET ether). A sample was submitted to chiral analytical HPLC analysis [Chiralpak AD, iso-hexane/iso-propanol: 8/2, 1 mL/min, 5.25 min (1$^{st}$ peak), 7.43 min (2$^{nd}$ peak), 99% e.e., absolute configuration not determined]. The chiral reaction product cis-tert-butyl) 1-(2-tert-butoxyphenyl)-3-(pyridin-2-yl)aziridine-2-carboxylate was afforded as a colourless oil in a 82% yield. The trans- product was not detectable by NMR.

Example 2

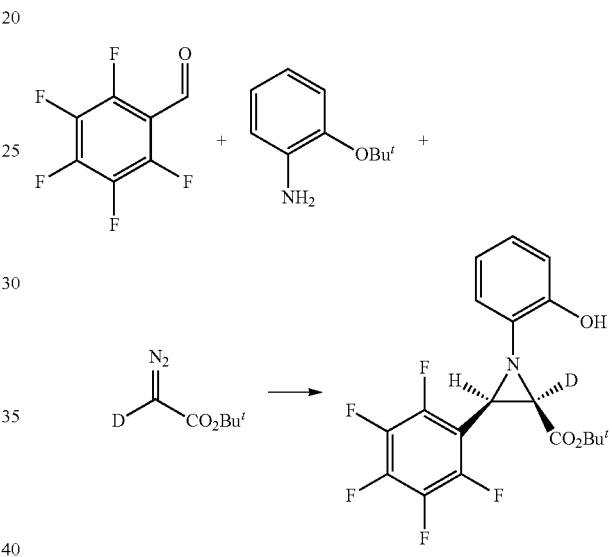

Pentafluorobenzaldehyde (40 mg, 0.26 mmol), O-tert-butoxy aniline (43 mg, 0.26 mmol), and catalyst (S)-3,3'-bis(9-anthracenyl)-[1,1']-binaphthalen-2,2'-yl-N-triflyl-phosphoramide (21.6 mg, 0.026 mmol, 10 mol %) were added to a flame dried biotage 2 mL microwave vial under nitrogen. 800 µL of deuterated chloroform was added (pre-dried over 4 Å molecular sieves), followed by ~40 mg of powdered 4 Å molecular sieves, and the vial was sealed with a PTFE crimp cap. 200 µL of anhydrous DCM was added via syringe through the septum, and the reaction mixture was cooled to −80° C. After 30 minutes, >95% α-deuterated tert-butyl diazoacetate (40 µL, 0.286 mmol) was added via syringe, and the reaction mixture was stirred at −80° C., monitoring by $^1$H-NMR until the reaction was deemed complete (~72 hours). At this point the reaction mixture was passed through a short plug of silica, eluting with diethyl ether. The solvents were removed under reduced pressure, and the residue was purified by flash chromatography (14% diethyl ether in PET ether). The product was a yellow oil afforded in an 82% yield. This was added to 1 mL acetonitrile and 500 µL of water was added, followed by para-toluene sulphonic acid (17 mg, 0.087 mmol). The resulting mixture was heated to 65° C. in a biotage creator microwave synthesiser, with stirring for 5 hours. After this time, the reaction mixture was neutralised by addition of a saturated aqueous solution of NaHCO$_3$. This was extracted with ethyl acetate, and the combined organic layers were washed with brine, dried with MgSO$_4$, filtered and the solvent removed under reduced pressure. The crude material was purified via column chromatography (30% diethyl ether in PET ether). The product cis-tert-butyl 1-(2-hydroxyphenyl)-3-(perfluorophenyl)aziridine-2-deutero-2-carboxylate was a slightly brown oil afforded in a 67% yield. A sample was submitted to chiral analytical HPLC analysis [Chiralpak IA, CO$_2$/iso-propanol: 5%-50% over 9 min, 0.7 mL/min, 3.78 min (1$^{st}$ peak), 4.23 min (2$^{nd}$ peak), 92% e.e., absolute configuration not determined]. The trans- product was not detectable by NMR.

Example 3

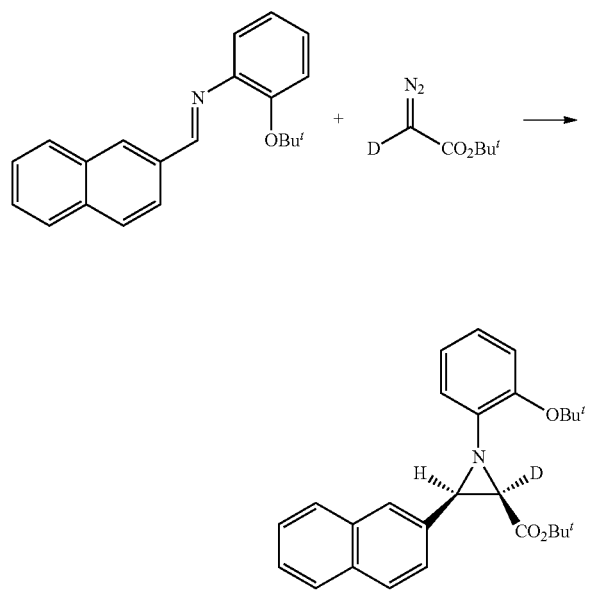

(E)-2-tert-Butoxy-N-(2-napthylmethylene)phenylamine (79 mg, 0.26 mmol), and catalyst (S)-3,3'-bis(9-anthracenyl)-[1,1']-binaphthalen-2,2'-yl-N-triflyl-phosphoramide (21.6 mg, 0.026 mmol, 10 mol %) were added to a flame dried Biotage 2 mL microwave vial under nitrogen. 800 µL of deuterated chloroform was added (pre-dried over 4 Å molecular sieves), and the vial was sealed with a PTFE crimp cap. 200 µL of anhydrous DCM was added via syringe through the septum, and the reaction mixture was cooled to −80° C. After 30 minutes, >95% α-deuterated tert-butyl diazoacetate (40 µL, 0.286 mmol) was added via syringe, and the reaction mixture was stirred at −80° C., monitoring by $^1$H-NMR until the reaction was deemed complete. At this point the reaction mixture was passed through a short plug of silica and eluted with diethyl ether. The solvents were removed under reduced pressure, and the residue was purified by flash chromatography (14% diethyl ether in PET). A sample was submitted to chiral analytical HPLC analysis [Chiralpak AD, iso-hexane/iso-propanol: 95/5, 1 mL/min, 4.61 min (1$^{st}$ peak), 11.01 min (2$^{nd}$ peak), 90% e.e., absolute configuration not determined]. 2-Deutero-cis-tert-butyl-1-(2-tert-butoxyphenyl)-3-(naphthalen-2-yl)aziridine-2-carboxylate was afforded as a yellow oil in an 85% yield. The trans- product was not detectable by NMR.

Example 4

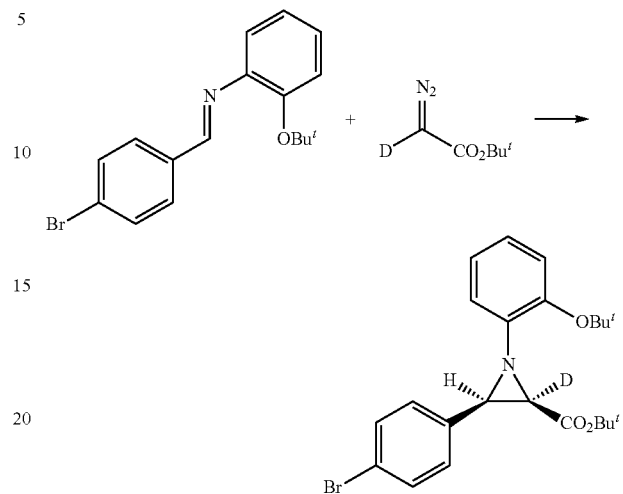

(E)-2-tert-Butoxy-N-(4-bromophenylmethylene)phenylamine (85 mg, 0.26 mmol), and catalyst (S)-3,3'-bis(9-anthracenyl)-[1,1']-binaphthalen-2,2'-yl-N-triflyl-phosphoramide (21.6 mg, 0.026 mmol, 10 mol %) were added to a flame dried Biotage 2 mL microwave vial under nitrogen. 800 µL of deuterated chloroform was added (pre-dried over 4 Å molecular sieves), and the vial was sealed with a PTFE crimp cap. 200 µL of anhydrous DCM was added via syringe through the septum, and the reaction mixture was cooled to −80° C. After 30 minutes, >95% α-deuterated tert-butyl diazoacetate (40 µL, 0.286 mmol) was added via syringe, and the reaction mixture was stirred at −80° C., monitoring by $^1$H-NMR until the reaction was deemed complete. At this point the reaction mixture was passed through a short plug of silica and eluted with diethyl ether. The solvents were removed under reduced pressure, and the residue was purified by flash chromatography (14% diethyl ether in PET). A sample was submitted to chiral analytical HPLC analysts [Chiralpak AD, iso-hexane/iso-propanol: 95/5, 1 mL/min, 4.12 min (1$^{st}$ peak), 7.27 min (2$^{nd}$ peak), 95% e.e., absolute configuration not determined]. 2-Deutero-cis-tert-butyl-1-(2-tert-butoxyphenyl)-3-(4-bromophenyl)aziridine-2-carboxylate was afforded as a yellow oil in an 87% yield. The trans- product was not detectable by NMR.

Example 5

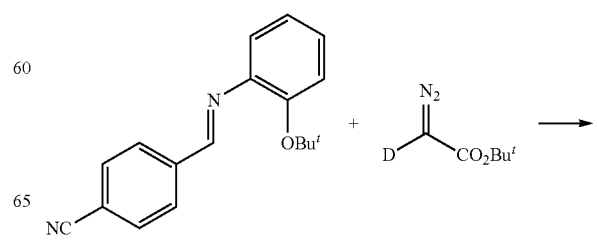

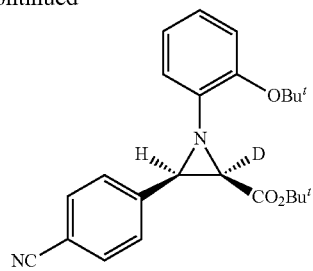

(E)-2-tert-Butoxy-N-(4-cyanophenylmethylene)phenylamine (72 mg, 0.26 mmol), and catalyst (S)-3,3'-bis(9-anthracenyl)-[1,1']-binaphthalen-2,2'-yl-N-triflyl-phosphoramide (21.6 mg, 0.026 mmol, 1.0 mol %) were added to a flame dried Biotage 2 mL microwave vial under nitrogen. 800 µL of deuterated chloroform was added (pre-dried over 4 Å molecular sieves), and the vial was sealed with a PTFE crimp cap. 200 µL of anhydrous DCM was added via syringe through the septum, and the reaction mixture was cooled to −80° C. After 30 minutes, >95% α-deuterated tert-butyl diazoacetate (40 µL, 0.286 mmol) was added via syringe, and the reaction mixture was stirred at −80° C., monitoring by $^1$H-NMR until the reaction was deemed complete. At this point the reaction mixture was passed through a short plug of silica and eluted with diethyl ether. The solvents were removed under reduced pressure, and the residue was purified by flash chromatography (14% diethyl ether in PET). A sample was submitted to chiral analytical HPLC analysis [Chiralpak AD, iso-hexane/iso-propanol: 95/5, 1 mL/min, 6.19 min ($1^{st}$ peak), 8.75 min ($2^{nd}$ peak), 99% e.e., absolute configuration not determined]. The 2-deutero-cis-tert-butyl-1-(2-tert-butoxyphenyl)-3-(4-cyanophenyl)aziridine-2-carboxylate was afforded as a yellow oil in a 65% yield. The trans- product was not detectable by NMR.

Example 6

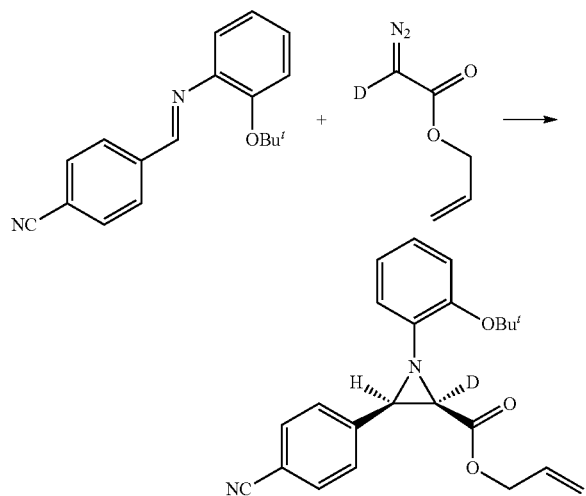

(E)-2-tert-Butoxy-N-(4-cyanophenylmethylene)phenylamine (74 mg, 0.26 mmol), and catalyst (S)-3,3'-bis(9-anthracenyl)-[1,1']-binaphthalen-2,2'-yl-N-triflyl-phosphoramide (21.6 mg, 0.026 mmol, 10 mol %) were added to a flame dried Biotage 2 mL microwave vial under nitrogen. 800 µL of deuterated chloroform was added (pre-dried over 4 Å molecular sieves), and the vial was sealed with a PTFE crimp cap. 200 µL of anhydrous DCM was added via syringe through the septum, and the reaction mixture was cooled to −80° C. After 30 minutes, >95% α-deuterated allyl diazoacetate (35 µL, 0.286 mmol) was added via syringe, and the reaction mixture was stirred at −80° C., monitoring by $^1$H-NMR until the reaction was deemed complete. At this point the reaction mixture was passed through a short plug of silica and eluted with diethyl ether. The solvents were removed under reduced pressure, and the residue was purified by flash chromatography (14% diethyl ether in PET ether). A sample was submitted to chiral analytical HPLC analysis [Chiralpak AD, iso-hexane/iso-propanol: 95/5, 1 mL/min, 12.20 min ($1^{st}$ peak), 20.4 min ($2^{nd}$ peak), 87% e.e., absolute configuration not determined]. The 2-deutero-cis-allyl-1-(2-tert-butoxyphenyl)-3-(4-cyanophenyl)aziridine-2-carboxylate was afforded as a yellow oil in a 68% yield. The trans- product was not detectable by NMR.

Example 7

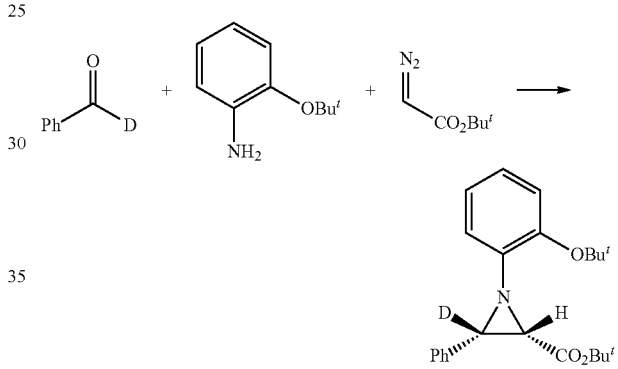

>95% Deuterated benzaldehyde (28 µL, 0.26 mmol), O-tert-butoxyaniline (43 mg, 0.26 mmol), and catalyst (R)-3,3'-bis(9-anthracenyl)-[1,1']-binaphthalen-2,2'-yl-N-triflyl-phosphoramide (21.6 mg, 0.026 mmol, 10 mol %) were added to a flame dried Biotage 2 mL microwave vial under nitrogen. 800 µL of deuterated chloroform was added (pre-dried over 4 Å molecular sieves), followed by ~40 mg powdered 4 Å molecular sieves, and the vial was sealed with a PTFE crimp cap. 200 µL of anhydrous DCM was added via syringe through the septum, and the reaction mixture was cooled to −80° C. After 30 minutes, tert-butyl diazoacetate (40 µL, 0.286 mmol) was added via syringe, and the reaction mixture was stirred at −80° C., monitoring by $^1$H-NMR until the reaction was deemed complete. At this point the reaction mixture was passed through a short plug of silica and eluted with diethyl ether. The solvents were removed under reduced pressure, and the residue was purified by flash chromatography (14% diethyl ether in PET ether). A sample was submitted to chiral analytical HPLC analysis [Chiralpak AD, iso-hexane/iso-propanol: 95/5, 1 mL/min, 3.77 min ($1^{st}$ peak), 7.10 min ($2^{nd}$ peak), 88% e.e., absolute configuration not determined]. 3-Deutero-cis-tert-butyl-1-(2-tert-butoxyphenyl)-3-phenylaziridine-2-carboxylate was afforded as a colourless oil in a 65% yield. The trans- product was not detectable by NMR.

From the above, it can be seen that the aziridination protocol disclosed herein has the following benefits:

1. It is extremely straightforward; the reagents are simply mixed and stirred.
2. In general there is no need to utilise dry solvents or inert atmospheres (unless either one of the starting materials is water sensitive), meaning that the system is cost efficient. Thus the process has a lower environmental/carbon footprint than conventional metal based protocols.
3. The starting materials are readily and cheaply available.
4. The asymmetric organocatalysts are highly efficient/active and can be utilised at low concentrations, even down to 0.1 mol %.
5. The catalysts should be recyclable, for instance by transferring them to a solid-support system allowing for facile removal after use. Immobilisation of the catalyst would also allow the synthesis of aziridines using flow technology or bed reactors.
6. The reaction conditions are extremely mild and the majority of commonly used functional and protecting groups are tolerated.
7. The aziridination protocol affords in many cases exceptionally high yields of product in exceptionally high stereoselectivities with no by-product formation.
8. The reaction process is environmentally benign, generating only nitrogen and water. Furthermore due to the high yields, the fact that no enamine or by-products are observed, and the fact that all of the starting materials are completely consumed, purification of the product is straightforward and uncomplicated.
9. The organocatalysts are easily generated and can be stored and used straight out of the bottle.
10. The procedure/catalysts are widely applicable to the transformation of structurally diverse starting materials into the corresponding aziridines; this contrasts with the relatively poor substrate specificity displayed by other reported catalysts.

Example 8

To compare the catalytic activity of the phosphoramide catalysts of the present invention to the catalytic activity of the equivalent phosphoric acid catalysts used by Akiyama et al. and Zeng et al. in the prior art as discussed above, the following experiment was performed:

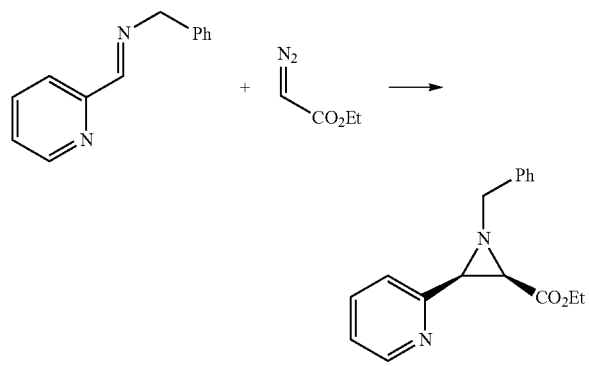

The aziridine formation outlined above was attempted using phosphoric acid based catalysts A, B and C, and also using phosphoramide catalyst D, all at 10 mol % in DCM at room temperature.

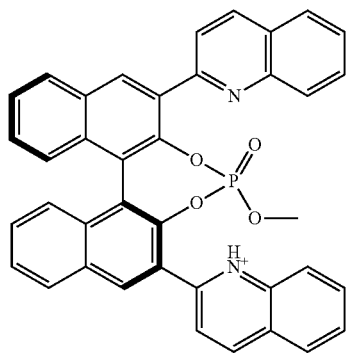

A

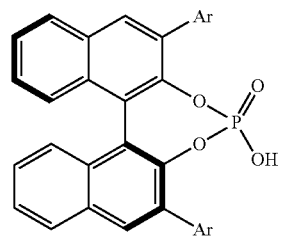

B

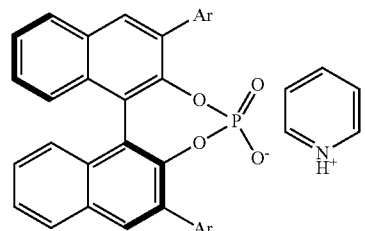

C

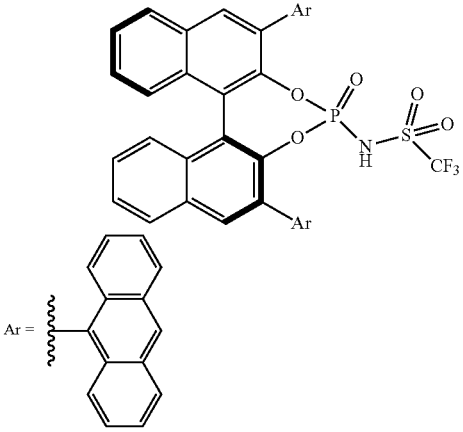

D

Using phosphoric acid catalyst A, the desired cis-aziridine was isolated in 16% yield, although the product was racemic by chiral HPLC analysis. Only trace amounts (<5% yield) of the desired cis-aziridine were found in the $^1$H-NMR spectra of the crude reaction mixtures when B or C was used as the catalyst.

In contrast, when the phosphoramide catalyst (S)-3,3'-bis (9-anthracenyl)-[1,1']-binaphthalen-2,2'-yl-N-triflyl-phosphoramide D was used, the reaction afforded the desired cis-aziridine in an 85% yield. Moreover, careful scrutinization of the $^1$H-NMR crude spectra proved that complete consumption of the starting imine had taken place and no traces of the trans-azridine were found in the crude reaction mixture. Analysis of the cis-aziridine produced using analytical chiral HPLC column confirmed that catalyst D had afforded the cis-aziridine in a 47% e.e.

Thus, it can be seen that under like-for-like conditions, the phosphoramide catalysts employed in the present invention afford superior yields and greater stereoselectivity than the equivalent phosphoric acid catalysts of the prior art.

Example 9

To compare the effect of the solvents utilised in the preferred embodiments of the present invention with those used by Hashimoto et al. in the journal article discussed above, the following experiment was performed:

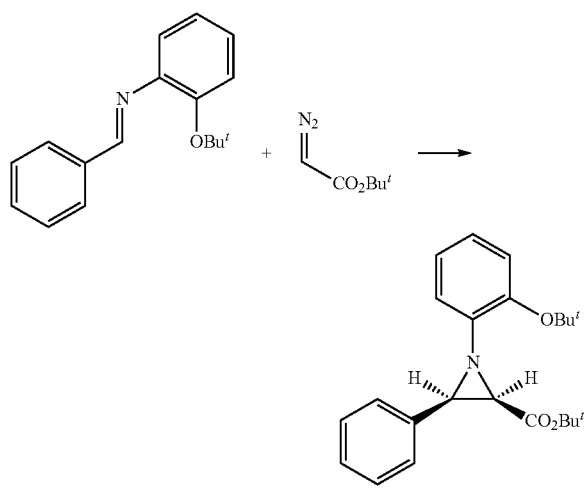

The aziridine formation outlined above was attempted using phosphoramide catalyst D at 10 mol % concentration at −78° C. in a range of solvents. Each solvent study was repeated to confirm reproducibility. The results are shown in the table below.

| | e.e. | | Molar yield | |
|---|---|---|---|---|
| Solvent | Study 1 | Study 2 | Study 1 | Study 2 |
| DCM | 39% | 47% | 81% | 82% |
| DCM:hexane (1:1) | 25% | 17% | 83% | 68% |
| Toluene | 19% | 22% | 87% | 80% |
| CHCl$_3$:DCM (8:2) | 84% | 90% | 87% | 74% |

Thus it can be seen that, under like-for-like conditions, the use of a reaction solvent comprising a mixture of halocarbons results in a marked increase in the stereoselectivity of the reaction versus the use of the solvent systems suggested in Hashimoto et al.

Example 10

To compare the effect of the reaction conditions utilised in the preferred embodiments of the present invention with those used by Hashimoto et al. in the journal article discussed above, the following experiment was performed:

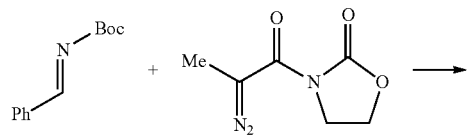

-continued

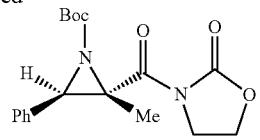

To a stirred solution of 3-(2-diazopropanoyl)oxazolidin-2-one (0.12 mmol, 20.0 mg) and benzaldehyde N-Boc imine (0.15 mmol, 31.6 mg) in CDCl$_3$/CD$_3$Cl$_2$ 8:2 mixture (0.8 mL) was added (S)-3,3'-bis(anthracen-9-yl)-[1,1']-binaphthalen-2,2'-yl-N-triflyl-phosphoramide (5.9 μmol, 4.9 mg, 5 mol %) in CDCl$_3$/CD$_2$Cl$_2$ 8:2 mixture (0.2 mL) at −78° C. under argon. The reaction mixture was stirred at the same temperature for 1 hour and then treated with triethylamine (20 μL). The mixture was poured into aqueous NaHCO$_3$ and extracted with ethyl acetate. The combined organic layers were dried over anhydrous MgSO$_4$ and concentrated in vacuo. The crude material was purified by column chromatography on silica gel (eluting with hexane/ethyl acetate/triethylamine, 4:1:0.05) to give tert-butyl 2-methyl-2-(2-oxooxazolidine-3-carbonyl)-3-phenylaziridine-1-carboxylate (29.7 mg, 72% yield) as a white solid. A single isomer was detectable by NMR. Enantiomeric purity was determined by HPLC analysis to be 90.7% e.e. (Column Cellulose-1, iso-hexane/iso-propanol=85:15, flow rate=1.0 ml/min, retention time=12.9 min (minor) and 22.4 min (major), column oven at 30° C.). The absolute configuration was not determined.

By comparison with entries 4 and 5 of Table 1 of Hashimoto et al., it can be seen that the reaction conditions of the present invention result in a substantial improvement in the enantiomeric excess of the aziridine obtained.

Example 11

To investigate the influence of solvent choice in the synthesis of isotopically labelled aziridines, the following experiment was performed:

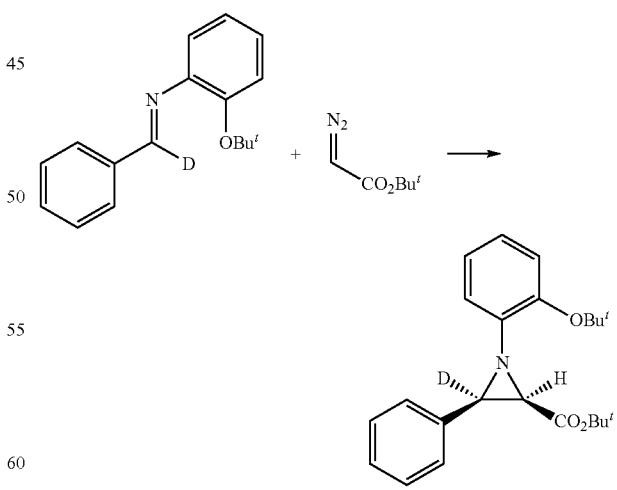

The aziridine formation outlined above was attempted using phosphoramide catalyst D at 10 mol % concentration at −78° C. in a range of solvents. Each solvent study was repeated to confirm reproducibility. The results are shown in the table below.

|         | e.e.    |         | Molar yield |         |
|---------|---------|---------|-------------|---------|
| Solvent | Study 1 | Study 2 | Study 1     | Study 2 |
| DCM              | 61% | 53% | 68% | 86% |
| DCM:hexane (1:1) | 59% | 59% | 88% | 71% |
| Toluene          | 79% | 69% | 86% | 79% |
| CHCl$_3$:DCM (8:2) | 88% | 82% | 91% | 91% |

Again, using a mixture of halocarbons a marked increase in the stereoselectivity of the reaction versus the use of the solvent systems suggested in Hashimoto et al. was observed.

Example 12

To further investigate the influence of solvent choice in the synthesis of isotopically labelled aziridines, the following experiment was performed:

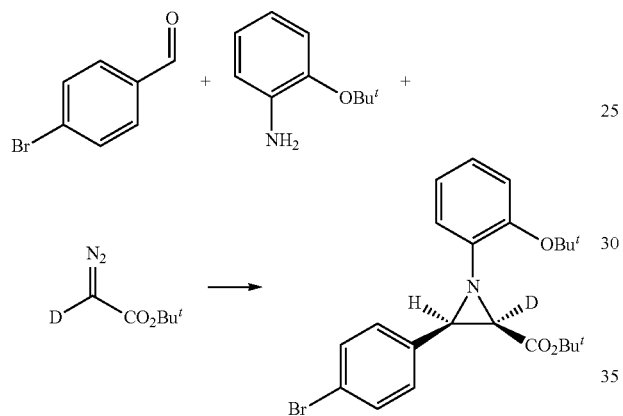

The aziridine formation outlined above was attempted using phosphoramide catalyst D at 10 mol % concentration in a range of solvents at various temperatures. The results are shown in the table below.

| Solvent | Temperature | e.e. | Molar yield |
|---------|-------------|------|-------------|
| DCM                | −70° C. | 79% | 80% |
| CHCl$_3$:toluene (1:1) | −80° C. | 83% | 73% |
| CHCl$_3$           | −63° C. | 82% | 87% |
| CHCl$_3$:DCM (8:2) | −80° C. | 92% | 85% |

Once again, it can be seen that by using a mixture of halocarbons as the reaction solvent, a marked increase in the stereoselectivity of the reaction is observed.

It will be understood that the present invention has been described above by way of example only. The examples are not intended to limit the scope of the present invention. Various modifications and embodiments can be made without departing from the scope and spirit of the invention, which is defined by the following claims only.

What is claimed is:

1. A method of synthesising aziridine (III) or a salt thereof, said method comprising contacting imine (I) or a salt, with a diazo compound (II) or a salt thereof, in a solvent comprising a mixture of halocarbons, in the presence of a catalyst:

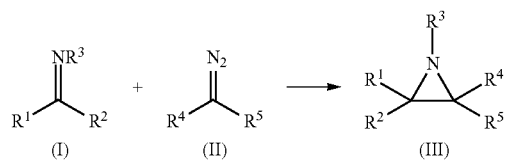

wherein $R^1$, $R^2$ and $R^3$ are each independently a hydrogen atom, a halogen atom or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein any two or more of $R^1$, $R^2$ and $R^3$ together with the atom or atoms to which they are attached may form a cyclic hydrocarbyl group which may optionally be substituted and which may optionally include one or more heteroatoms N, O or S in its carbon skeleton;

wherein $R^4$ and $R^5$ are each independently a hydrogen atom, a halogen atom or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton, and wherein $R^4$ and $R^5$ together with the atom or atoms to which they are attached may form a cyclic hydrocarbyl group which may optionally be substituted and which may optionally include one or more heteroatoms N, O or S in its carbon skeleton;

wherein the catalyst is a compound of formula (IV) or a salt thereof:

wherein:
X is O;
$R^6$ is —SO$_2$—$R^e$;
$R^e$ is a substituted or unsubstituted, straight-chain, branched or cyclic alkyl, alkenyl, aryl, arylalkyl, arylalkenyl, alkylaryl, or alkenylaryl group which optionally includes one or more heteroatoms in its carbon skeleton;
$R^7$ and $R^8$ together form a chiral bidentate ligand of formula (VIb), (VIb') or (VIb"):

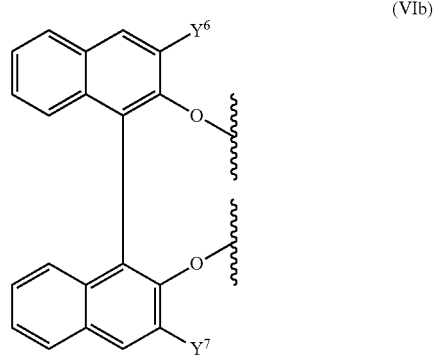

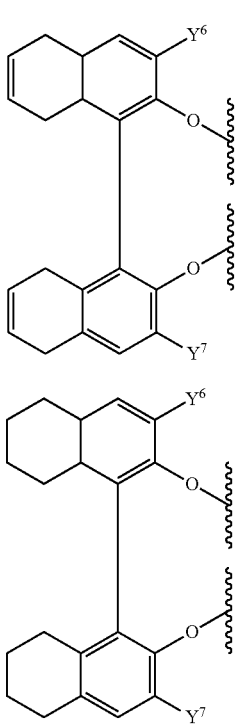

wherein $Y^6$ and $Y^7$ are each independently selected from a substituted or unsubstituted aryl or alkylaryl group which optionally includes one or more heteroatoms in its carbon skeleton;

and wherein optionally the imine (I), and/or the diazo compound (II) are isotopically labelled such that the resultant aziridine (III) is also isotopically labelled.

2. The method as claimed in claim 1, wherein the imine (I), and/or the diazo compound (II) are isotopically labelled such that the resultant aziridine (III) is also isotopically labelled.

3. The method as claimed in claim 1, wherein:
(i) the method comprises contacting the imine (I) or the salt thereof with the diazo compound (II) or the salt thereof; or
(ii) the method comprises contacting the imine (I) or the salt thereof with the diazo compound (II) or the salt thereof, and wherein the method further comprises the step of synthesising the imine (I) or the salt thereof from an amine $H_2NR^3$ or a salt thereof, and a carbonyl compound $R^1COR^2$ or a salt thereof; or
(iii) the method comprises contacting the imine (I) or the salt thereof with the diazo compound (II) or the salt thereof, and wherein the method further comprises the step of synthesising the imine (I) or the salt thereof from an amine $H_2NR^3$ or a salt thereof, and a carbonyl compound $R^1COR^2$ or a salt thereof, wherein the imine (I) or the salt thereof is not isolated.

4. The method as claimed in claim 1, wherein $R^1$, $R^2$ and $R^3$ are each independently hydrogen atoms or comprise from 1 to 12 carbon atoms.

5. The method as claimed in claim 1, wherein:
(i) $R^1$ is a hydrogen atom or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton; and/or
(ii) $R^2$ is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton; and/or
(iii) $R^3$ is a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

6. The method as claimed in claim 1, wherein:
(i) $R^1$ is a hydrogen atom or a substituted or unsubstituted alkyl, alkenyl, acyl, aryl, arylalkyl or alkylaryl group which optionally includes one or more heteroatoms in its carbon skeleton; and/or
(ii) $R^2$ is a substituted or unsubstituted aryl, arylalkyl, arylalkenyl, arylalkynyl, alkylaryl, alkenylaryl or alkynylaryl group which optionally includes one or more heteroatoms in its carbon skeleton; and/or
(iii) $R^3$ is a substituted or unsubstituted alkyl, alkenyl, acyl, aryl, arylalkyl or alkylaryl group which optionally includes one or more heteroatoms in its carbon skeleton.

7. The method as claimed in claim 6, wherein:
(i) $R^1$ is $^1H$, $^2H$ or $^3H$; and/or
(ii) $R^2$ is a substituted or unsubstituted aryl group which optionally includes one or more heteroatoms in its carbon skeleton; and/or
(iii) $R^3$ is a substituted or unsubstituted acyl, aryl, arylalkyl or alkylaryl group which optionally includes one or more heteroatoms in its carbon skeleton.

8. The method as claimed in claim 1, wherein $R^1$ is a hydrogen atom, $R^2$ is a substituted or unsubstituted alkyl, acyl, aryl, arylalkyl or alkylaryl group which optionally includes one or more heteroatoms in its carbon skeleton, and $R^3$ is a substituted or unsubstituted alkyl, alkenyl, aryl, arylalkyl or alkylaryl group which optionally includes one or more heteroatoms in its carbon skeleton.

9. The method as claimed in claim 1, wherein $R^4$ and $R^5$ are each independently a hydrogen atom or a substituted or unsubstituted, straight-chain, branched or cyclic alkyl, alkenyl, acyl, aryl, arylalkyl or alkylaryl group which optionally includes one or more heteroatoms in its carbon skeleton.

10. The method as claimed in claim 1, wherein at least one of $R^4$ and $R^5$ is a $-NO_2$, $-CN$, $-CO-R^d$, $-CO-OR^d$, $-CO-N(R^d)_2$, $-CS-R^d$, $-CS-OR^d$, $-CS-N(R^d)_2$, $-C=NR^d-N(R^d)_2$, $-C=NR^d-R^d$ or $-C=NR^d-OR^d$ group, wherein each $-R^d$ is independently hydrogen or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

11. The method as claimed in claim 9, wherein at least one of $R^4$ and $R^5$ is a $-CO-R^d$, $-CO-OR^d$, or $-CO-N(R^d)_2$ group, wherein each $-R^d$ is independently a hydrogen atom or a substituted or unsubstituted, straight-chain, branched or cyclic alkyl, alkenyl, alkynyl, acyl, aryl, arylalkyl, arylalkenyl, arylalkynyl, alkylaryl, alkenylaryl or alkynylaryl group which optionally includes one or more heteroatoms in its carbon skeleton.

12. The method as claimed in claim 11, wherein at least one of $R^4$ and $R^5$ is a —CO—$OR^d$ group, wherein $R^d$ is an unsubstituted alkyl or alkenyl group comprising from 1 to 6 carbon atoms or an unsubstituted arylalkyl group comprising from 7 to 12 carbon atoms.

13. The method as claimed in claim 1, wherein $R^6$ is —$SO_2CF_3$.

14. The method as claimed in claim 1, wherein $Y^6$ and $Y^7$ are each independently selected from a substituted or unsubstituted fused aryl group, which optionally includes one or more heteroatoms in its carbon skeleton.

15. The method as claimed in claim 1, wherein $R^7$ and $R^8$ together form a chiral bidentate ligand of formula (VIb):

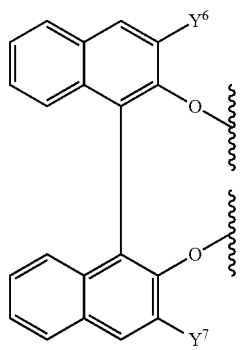

wherein $Y^6$ and $Y^7$ are the came and are selected from

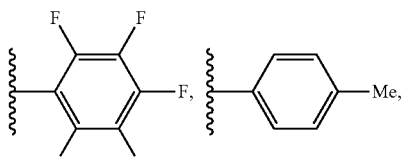

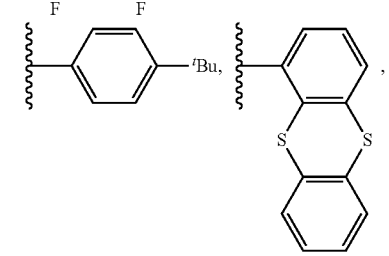

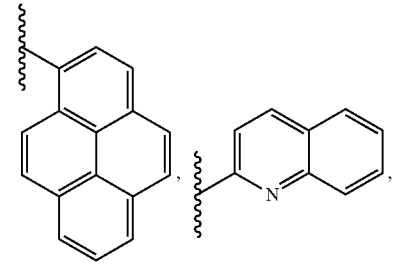

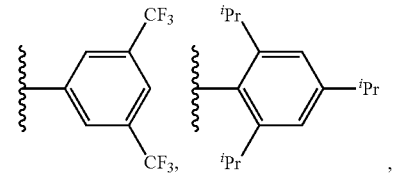

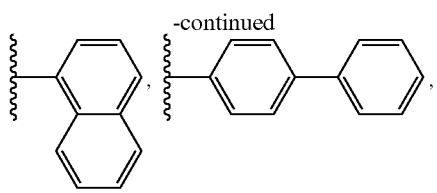

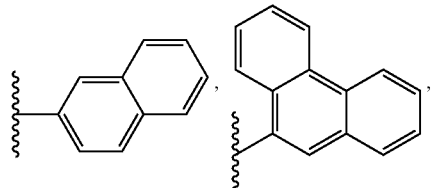

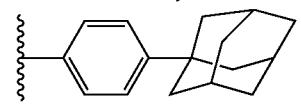

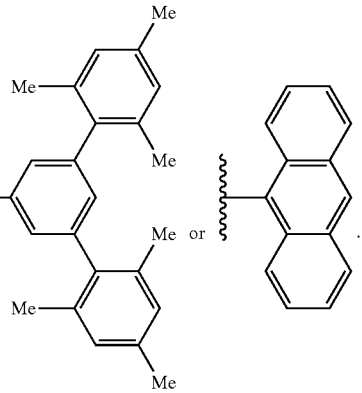

16. The method as claimed in claim 1, wherein:
   (i) at least one of $R^1$, $R^2$, $R^3$, $R^4$ and $R^5$ is $^2H$ or $^3H$; and/or
   (ii) $R^1$ and/or $R^4$ are $^2H$ or $^3H$; and/or
   (iii) the nitrogen atom of the C=N group of the imine (I) is $^{15}N$, such that the nitrogen atom in the aziridine ring of (III) is $^{15}N$; and/or
   (iv) the carbon atom of the C=N group of the imine (I), and/or the carbon atom of the C=$N_2$ group of the diazo compound (II) is $^{13}C$ or $^{14}C$, such that one or both of the carbon atoms in the aziridine ring of (III) is $^{13}C$ or $^{14}C$.

17. The method as claimed in claim 1, wherein:
   (i) $R^1$ and $R^4$ in the aziridine (III) are mostly cis- or mostly trans-; and/or
   (ii) the synthesis of the aziridine (III) is enantioselective.

18. The method as claimed in claim 1, wherein the solvent is a mixture of chloroform and dichloromethane, optionally wherein the chloroform and/or the dichloromethane is labelled with $^2H$ or $^3H$.

19. The method as claimed in claim 18, wherein:
   (i) the ratio of chloroform:dichloromethane in the solvent mixture is from 50:50 to 95:5 by volume; or
   (ii) the ratio of chloroform:dichloromethane in the solvent mixture is from 70:30 to 90:10 by volume.

20. The method as claimed in claim 1, wherein the method further comprises the steps of:
   (a) chemically modifying or cleaving any of $R^1$, $R^2$, $R^3$, $R^4$ or $R^5$ to give a modified aziridine or a salt thereof; and/or (b) ring-opening or ring-expanding the aziridine (III) or the modified aziridine to give an aziridine-derived compound or a salt thereof.

21. The method as claimed in claim 1, wherein the solvent is a mixture of chlorocarbons.

* * * * *

UNITED STATES PATENT AND TRADEMARK OFFICE
CERTIFICATE OF CORRECTION

PATENT NO.        : 10,259,784 B2
APPLICATION NO.   : 15/675982
DATED             : April 16, 2019
INVENTOR(S)       : Sean Patrick Bew and Sean Michael Thurston It is certified that error appears in the above-identified patent and that said Letters Patent is hereby corrected as shown below:

In the Claims

In Column 47, Line 32 of Claim 15, please delete "wherein Y6 and Y7 are the came and are selected from" and replace with --wherein Y6 and Y7 are the same and are selected--.

Signed and Sealed this
Ninth Day of July, 2019

Andrei Iancu
*Director of the United States Patent and Trademark Office*

UNITED STATES PATENT AND TRADEMARK OFFICE
CERTIFICATE OF CORRECTION

PATENT NO. : 10,259,784 B2
APPLICATION NO. : 15/675982
DATED : April 16, 2019
INVENTOR(S) : Sean Patrick Bew et al.

It is certified that error appears in the above-identified patent and that said Letters Patent is hereby corrected as shown below:

In the Claims

In Column 47, Line 32 of Claim 15, please delete "wherein Y6 and Y7 are the same and are selected" and replace with --wherein Y6 and Y7 are the same and are selected from--.

Signed and Sealed this
Twentieth Day of August, 2019

Andrei Iancu
*Director of the United States Patent and Trademark Office*